(12) United States Patent
Martin et al.

(10) Patent No.: US 7,786,176 B2
(45) Date of Patent: Aug. 31, 2010

(54) VAGINAL TREATMENT COMPOSITION CONTAINING XYLITOL

(75) Inventors: Stephanie M. Martin, Woodstock, GA (US); Lei Huang, Duluth, GA (US); Shu-Ping Yang, Alpharetta, GA (US); Yanbin Huang, Foster City, CA (US); Julie Villanueva, Decatur, GA (US); Sharon Linda Greene, Canton, GA (US); Kelly Arehart, Roswell, GA (US); Curtis Sayre, Atlanta, GA (US); Robert B. Johnson, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 591 days.

(21) Appl. No.: 11/194,064

(22) Filed: Jul. 29, 2005

(65) Prior Publication Data
US 2007/0026074 A1 Feb. 1, 2007

(51) Int. Cl.
*A61K 31/045* (2006.01)
(52) U.S. Cl. .................. 514/738; 514/724; 514/576; 424/430
(58) Field of Classification Search ................. None
See application file for complete search history.

(56) References Cited

U.S. PATENT DOCUMENTS

| | | | |
|---|---|---|---|
| 3,812,250 A | 5/1974 | Aubert et al. |
| 3,860,707 A | 1/1975 | Wootton |
| 4,094,647 A | 6/1978 | Deutsch et al. |
| 4,168,146 A | 9/1979 | Grubb et al. |
| 4,326,052 A | 4/1982 | Kang et al. |
| 4,326,053 A | 4/1982 | Kang et al. |
| 4,377,636 A | 3/1983 | Kang et al. |
| 4,385,123 A | 5/1983 | Kang et al. |
| 4,542,020 A | 9/1985 | Jackson et al. |
| 4,563,366 A | 1/1986 | Baird et al. |
| 4,795,642 A | 1/1989 | Cohen et al. |
| 4,815,843 A | 3/1989 | Tiefenthaler et al. |
| 4,818,710 A | 4/1989 | Sutherland et al. |
| RE33,581 E | 4/1991 | Nicoli et al. |
| 5,124,254 A | 6/1992 | Hewlins et al. |
| 5,190,927 A | 3/1993 | Chang et al. |
| 5,196,350 A | 3/1993 | Backman et al. |
| 5,330,898 A | 7/1994 | Bar-Or et al. |
| 5,346,703 A | 9/1994 | Viegas et al. |
| 5,496,701 A | 3/1996 | Pollard-Knight |
| 5,527,892 A | 6/1996 | Borsotti et al. |
| 5,531,982 A | 7/1996 | Gaffar et al. |
| 5,624,537 A | 4/1997 | Turner et al. |
| 5,654,027 A | 8/1997 | Chalupa |
| 5,698,214 A | 12/1997 | Leveen et al. |
| 5,700,636 A | 12/1997 | Sheiness et al. |
| 5,733,572 A | 3/1998 | Unger et al. |
| 5,770,543 A | 6/1998 | Garst et al. |
| 5,840,338 A | 11/1998 | Roos et al. |
| 5,998,176 A | 12/1999 | Budolfsen et al. |
| 6,013,698 A | 1/2000 | Lupton et al. |
| 6,042,854 A | 3/2000 | Morris et al. |
| 6,066,677 A | 5/2000 | Uhari et al. |
| 6,093,394 A | 7/2000 | Chrisope |
| 6,117,090 A | 9/2000 | Caillouette |
| 6,136,287 A | 10/2000 | Horne et al. |
| 6,136,298 A | 10/2000 | Gaffar et al. |
| 6,159,491 A | 12/2000 | Durrani |
| 6,159,703 A | 12/2000 | Menton et al. |
| 6,174,524 B1 | 1/2001 | Bawa et al. |
| 6,210,695 B1 | 4/2001 | Beerse et al. |
| 6,234,974 B1 | 5/2001 | Catt et al. |
| 6,251,436 B1 | 6/2001 | Drizen et al. |
| 6,255,066 B1 | 7/2001 | Louderback |
| 6,346,272 B1 | 2/2002 | Viegas et al. |
| 6,395,298 B1 | 5/2002 | Flannagan et al. |
| 6,407,051 B1 | 6/2002 | Smith et al. |
| 6,414,035 B1 | 7/2002 | Vargas Munita et al. |
| 6,419,913 B1 | 7/2002 | Niemiec et al. |
| 6,432,440 B1 | 8/2002 | Watts et al. |
| 6,432,892 B2 | 8/2002 | Meine et al. |
| 6,440,949 B1 | 8/2002 | Zeng |
| 6,486,213 B1 | 11/2002 | Chen et al. |
| 6,514,950 B1 | 2/2003 | Baschong et al. |
| 6,519,355 B2 | 2/2003 | Nelson |
| 6,537,538 B2 | 3/2003 | Zaneveld et al. |
| 6,551,584 B2 | 4/2003 | Bandyopadhyay et al. |
| 6,562,363 B1 | 5/2003 | Mantelle et al. |

(Continued)

FOREIGN PATENT DOCUMENTS

BE 523649 10/1953

(Continued)

OTHER PUBLICATIONS

Chang et al, "Rheological evaluation of thermosensitive and mucoadhesive vaginal gels in phyisiological conditions" International Journal of Pharmaceutics, 2002, vol. 241, pp. 155-163.*

(Continued)

*Primary Examiner*—Allison M Ford
(74) *Attorney, Agent, or Firm*—Dority & Manning, P.A.

(57) ABSTRACT

A vaginal treatment composition that rapidly forms a gel when placed into contact with monovalent or polyvalent cations, such as sodium ($Na^+$) and calcium ($Ca^{2+}$) cations naturally found in vaginal mucosa, is provided. The gel may form in less than about 1 hour, in some embodiments less than about 1 minute, and in some embodiments, less than about 30 seconds. Among other things, such rapid gelation reduces the likelihood of leakage during use. In addition, because the gel may form intravaginally, it is more likely to retain its structure and shape over an extended period of time. In this manner, the gel may provide the prolonged release of a therapeutic agent that inhibits and/or treats vaginal infection. For instance, the gel may remain within the vagina for about 2 to about 48 hours to provide the desired effect.

15 Claims, 7 Drawing Sheets

U.S. PATENT DOCUMENTS

| | | | |
|---|---|---|---|
| 6,567,693 | B1 | 5/2003 | Allen, Jr. |
| 6,585,966 | B2 | 7/2003 | Kojima |
| 6,593,292 | B1 | 7/2003 | Rothbard et al. |
| 6,602,996 | B1 | 8/2003 | Sworn et al. |
| 6,645,181 | B1 | 11/2003 | Lavi et al. |
| 6,652,842 | B2 | 11/2003 | Lucia et al. |
| 6,653,263 | B1 | 11/2003 | Küpper et al. |
| 6,656,913 | B1 | 12/2003 | Resheski-Wedepohl et al. |
| 6,706,276 | B2 | 3/2004 | Garg et al. |
| 6,716,819 | B2 | 4/2004 | Welsh et al. |
| 6,759,382 | B2 | 7/2004 | Ahmed |
| 6,777,003 | B1 | 8/2004 | Desai et al. |
| 6,809,068 | B1 | 10/2004 | Küpper et al. |
| 6,825,234 | B2 | 11/2004 | Yeager et al. |
| 6,835,374 | B2 | 12/2004 | Parekh et al. |
| 6,861,066 | B2 | 3/2005 | Van de Casteele |
| 6,899,890 | B2 | 5/2005 | Kirschner et al. |
| 6,913,759 | B2 | 7/2005 | Borgman et al. |
| 6,946,490 | B2 | 9/2005 | Squires |
| 6,962,897 | B2 | 11/2005 | Küpper et al. |
| 6,979,464 | B2 | 12/2005 | Gutowska |
| 7,015,181 | B2 | 3/2006 | Lambino |
| 7,166,273 | B2 | 1/2007 | Chaudhuri |
| 7,258,878 | B2 | 8/2007 | Greene et al. |
| 2002/0044926 | A1 | 4/2002 | Reid et al. |
| 2002/0132008 | A1 | 9/2002 | Mumper et al. |
| 2002/0142042 | A1 | 10/2002 | Mumper et al. |
| 2002/0187181 | A1 | 12/2002 | Godbey et al. |
| 2003/0072803 | A1 | 4/2003 | Goldenberg et al. |
| 2003/0091641 | A1 | 5/2003 | Tiller et al. |
| 2003/0100078 | A1 | 5/2003 | Harding et al. |
| 2003/0143274 | A1 | 7/2003 | Viegas et al. |
| 2003/0143580 | A1 | 7/2003 | Straus |
| 2003/0143909 | A1 | 7/2003 | Barnabas et al. |
| 2003/0157587 | A1 | 8/2003 | Gomez et al. |
| 2003/0175333 | A1 | 9/2003 | Shefer et al. |
| 2003/0181384 | A1 | 9/2003 | Podolsky |
| 2003/0204180 | A1 | 10/2003 | Huang et al. |
| 2003/0225034 | A1 | 12/2003 | Floros et al. |
| 2004/0009725 | A1 | 1/2004 | Yahiaoui et al. |
| 2004/0147189 | A1 | 7/2004 | Smith, III et al. |
| 2004/0168920 | A1 | 9/2004 | Thorne et al. |
| 2004/0180800 | A1 | 9/2004 | McMahan |
| 2004/0242535 | A1* | 12/2004 | Court et al. .................. 514/54 |
| 2005/0084534 | A1 | 4/2005 | Ni et al. |
| 2005/0085739 | A1 | 4/2005 | MacDonald et al. |
| 2005/0089539 | A1 | 4/2005 | Scholz et al. |
| 2005/0137272 | A1 | 6/2005 | Gaserod et al. |
| 2005/0220882 | A1 | 10/2005 | Pritchard et al. |
| 2006/0045912 | A1 | 3/2006 | Truog |
| 2007/0264206 | A1 | 11/2007 | Boga et al. |

FOREIGN PATENT DOCUMENTS

| | | |
|---|---|---|
| EP | 0535534 A1 | 4/1993 |
| EP | 1072268 A1 | 1/2001 |
| EP | 1254206 B1 | 11/2002 |
| EP | 1310234 A2 | 5/2003 |
| EP | 1310234 A3 | 5/2003 |
| EP | 1417953 A2 | 5/2004 |
| FR | 2679773 A1 | 2/1993 |
| GB | 2173400 A | 10/1986 |
| WO | WO 9307249 A1 | 4/1993 |
| WO | WO 9403150 A1 | 2/1994 |
| WO | WO 9819545 A1 | 5/1998 |
| WO | WO 9823292 | 6/1998 |
| WO | WO 9927922 A1 | 6/1999 |
| WO | WO 0050891 A1 | 8/2000 |
| WO | WO 0159059 A1 | 8/2001 |
| WO | WO 0166084 A2 | 9/2001 |
| WO | WO 02092049 A2 | 11/2002 |
| WO | WO 02092049 A3 | 11/2002 |
| WO | WO 03031557 A1 | 4/2003 |
| WO | WO 2004078122 A2 | 9/2004 |
| WO | WO 2004078122 A3 | 9/2004 |
| WO | WO 2004110461 A1 | 12/2004 |
| WO | WO 2005051365 A1 | 6/2005 |
| WO | WO 2006047590 A2 | 5/2006 |
| WO | WO 2006047590 A3 | 5/2006 |

OTHER PUBLICATIONS

Pformulate, "Excipients: Gellan Gum." Jan. 25, 2004 (retrieved from URL: http://www.pformulate.com/gellangum.htm on Jan. 22, 2010) (2 pages).*
Article—*From a Doctor to a Doctor*, J. T. Weeks, The Mississippi Doctor, vol. 32, No. 2, Jun. 1954-May 1955, pp. 56-57.
Article—*Adhesion of Gardnerelle vaginalis to vaginal epithelial cells: variables affecting adhesion and inhibition by metronidazole*, Peeters et al., Genitourin Med., vol. 61, 1985, pp. 391-395.
Article—*Specificity and Mechanism of* In Vitro *Adherence of Candida albicans*, Reinhart, et al., Annals of Clinical and Laboratory Science, vol. 15, No. 5, 1985, pp. 406-413.
Search Report and Written Opinion for PCT/US2005/040842, Apr. 6, 2006.
PCT Search Report for Int'l Appl. No. PCT/US2006/01918 date of mailing Feb. 16, 2007.
U.S. Appl. No. 10/987,463, filed Nov. 12, 2004, Yang et al., A Compound and Method for Prevention and/or Treatment of Vaginal Infections.
U.S. Appl. No. 11/091,205, filed Mar. 28, 2005, Huang et al., A Method for Preventing and/or Treating Vaginal and Vulval Infections.
U.S. Appl. No. 11/091,206, filed Mar. 28, 2005, Huang et al., A Method for Preventing and/or Treating Trichomonas Vaginitis.
U.S. Appl. No. 11/094,496, filed Mar. 30, 2005, Huang et al., Method for Inhibiting and/or Treating Vaginal Infection.
U.S. Appl. No. 11/194,039, filed Jul. 29, 2005, Yang et al., Therapeutic Agents for Inhibiting and/or Treating Vaginal Infection.
Abstract of Japanese Patent No. JP2002226385, Aug. 14, 2002.
Article—*A Vaginal Fluid Simulant*, Owen et al., Contraception, vol. 59, Feb. 1999, pp. 91-95.
Article—*Alkyl Polyglycosides. A New Surfactant Class Based on Renewable Raw Material*, Knaut et al., Chimicaoggi, Sep. 1993, 6 pages.
Article—*Alkyl Polyglycosides—Properties and Applications of a new Class of Surfactants*, Rybinski et al., Angew. Chem. Int. Ed., vol. 37, 1998, pp. 1328-1345.
Article—*Amine Content of Vaginal Fluid from Untreated and Treated Patients with Nonspecific Vaginitis*, Chen et al., The Journal of Clinical Investigation., vol. 63, May 1979, pp. 828-835.
Article—*Biochemical Diagnosis of Vaginitis: Determination of Diamines in Vaginal Fluid*, Chen et al., The Journal of Infectious Diseases, vol. 145, No. 3, Mar. 1982, pp. 337-345.
Article—*Effect of long-term, peroral administration of sugar alcohols on man*, Kauko K. Mäkinen, Swed Dent J, vol. 8, 1984, pp. 113-124.
Article—*Sugar-based surfactants for consumer products and technical applications*, Hill et al., Feu/Lipid, vol. 101, 1999, pp. 25-33.
Article—*The scope and potential of vaginal drug delivery*, Vermani et al., Pharm. Sci. Tehnol. Today, Oct. 1, 2000, vol. 3, No. 10, pp. 359-364.
Fact Sheet on Trichomonas Infection from CDC—Division of Parasitic Diseases, 5 pages, Sep. 2004, www.cdc.com.
Information—Vaginal Infections from StopGettingSick.com, 2 pages, Aug. 2005, www.stopgettingsick.com.
Product Information on Triton* BG-10 Surfactant from DOW Surfactants, 2 pages.
Product Information on Triton* CG-110 Surfactant from DOW Surfactants, 2 pages.
Article—*Cloning and characterization of a gene (LIP1) which encodes a lipase from the pathogenic yeast Candida albicans*, Fu et al., Microbiology, vol. 143, 1992, pp. 331-340.
Article— In vitro *antimicrobial activity of extracts and isolated constituents of Rubus ulmifolius*, Panizzi et al., Journal of Ethnopharmacology, vol. 79, 2002, pp. 165-168.

Article—*Resolution of Resistant Vaginal Trichomoniasis Associated with the Use of Intravaginal Nonoxynol-9*, Livengood, III et al., Obstetrics & Gynecology, vol. 78, No. 5, Part 2, Nov. 1991, 954-956.

Article—*The susceptibility of organisms associated with bacterial vaginosis to spermicidal compounds*, in vitro, Jones et al., Genitourin. Med., vol. 67, 1991, pp. 475-477.

Search Report and Written Opinion for PCT/US2006/003681.

Article—*Bioactive ellagitannins from Cunonia macrophylla, an endemic Cunoniaceae from New Caledonia*, Fogliani et al., Phytochemistry, vol. 66, Elsevier Ltd., 2005, pp. 241-247.

Article—*Antimicrobial Properties of Aromatic Compounds of Plant Origin*, Zemek et al., Folia Microbiology, vol. 32, No. 5, 1987, pp. 421-425.

Article—*Effect of Gallic Acid and Catechin on Lactobacillus Hilgardii 5w Growth and Metabolism of Organic Compounds*, Alberto et al., Journal of Agriculture and Food Chemistry, vol. 49, 2001, pp. 4359-4363.

* cited by examiner

VAGINAL TREATMENT COMPOSITION CONTAINING XYLITOL

BACKGROUND OF THE INVENTION

The female vagina is naturally colonized by a variety of bacteria, yeast, and microorganisms. For example, a normal vagina generally contains more than about $10^4$ *lactobacilli* per milliliter of vaginal fluid. Under normal conditions, the vagina flora provides a mildly acidic environment that helps guard against the invasion of pathogenic microbes. Unfortunately, this vaginal balance may be easily upset by a variety of external factors that ultimately lead to vaginal infection. Vaginal infection is a clinical syndrome and exists in three primary forms, i.e., bacterial vaginosis, candidal vaginitis ("yeast"), and trichomonas vaginitis ("trich").

Bacterial vaginosis, for example, is a polymicrobial vaginal infection believed to be caused by an increase in the number of anaerobic organisms with a concomitant decrease in *lactobacilli* in the vagina. The decrease in the number of *lactobacilli* in the vagina has the dual effect of decreasing competition for nutrients and decreasing the amount of lactic acid present (i.e., increasing the pH). This allows for the multiplication of opportunistic pathogens in the vagina, whose growth is normally suppressed by the *lactobacilli* and the acidic pH of the vagina. The principal pathogen associated with bacterial vaginosis is believed to be *Gardnerella vaginalis*. Symptoms of bacterial vaginosis generally include an unpleasant smell, an elevated vaginal pH greater than about 5.0, a thin homogeneous discharge, and the presence of *Gardnerella* clue cells (i.e., vaginal epithelial cells coated with small Gram-variable rods). Current treatment regimens for bacterial infection of the vagina involve the use of various broad spectrum antibiotics, such as metronidazole. However, antibiotics are often undesirable because they may kill a broad range of the normal bacterial flora in the vagina, including the beneficial *lactobacilli*. This may cause secondary complications, because the *lactobacilli* keep various opportunistic pathogens in the vagina in check. The treatment may then necessitate a further treatment regimen, such as the ingestion of cultured dairy products to replace the *lactobacilli* in the body, as well as treatment by antifungal agents. Moreover, a rise in the level of anaerobes due to a lack of *lactobacilli* could further complicate the infection. Additionally, antibiotics, when used frequently within the vagina, may cause systemic toxicity through absorption from the vagina.

In addition, trichomonas vaginitis (or "trich") is one of the most common vaginal infections and is considered a sexually transmitted disease. Symptoms of trichomonas vaginitis include vulvar itching and odorous vaginal discharge. Trichomonas vaginitis is caused by *Trichomonas vaginalis*, a single-celled protozoan parasite not normally found in the flora of the genitourinary tract. *Trichomonas vaginalis* is a flagellate protozoa that is pear-shaped and about the size of a white blood cell. These motile cells have four flagellae and a single nucleus. Like bacterial vaginosis, this pathology is generally treated with metronidazole.

Further, the yeast *Candida albicans* causes the disease known as candidiasis (or "thrush"), as well as vulvitis (or "vulval" infection). *Candida albicans* is present in most humans as a harmless commensal organism. Problems arise, however, when a person experiences a loss of normal bacterial flora. In severely immune compromised patients, for example, *Candida albicans* infection may spread throughout the body and cause systemic infections. Candidiasis is usually treated with fluconazole, but this may have serious side effects and is not recommended for use during pregnancy.

In view of the some of the problems discussed above, various alternative treatment regimens have been developed. For example, one regimen for treating vaginal infection includes the repeated application of intra-vaginal cream or gel over a period of several days to about a week. However, many conventional cream or gel compositions readily leak from the vagina, thereby causing an undesirable feel for the user. The leakage of the gel also causes the therapeutic agent to break contact with the vaginal tissue after only a short period of time, thus reducing its potential effectiveness against vaginal infection. Another problem with some gels is that they prematurely gel. For instance, the formation of certain gels is induced by a change in temperature (i.e. thermogels). Unfortunately, during storage or shipping, these gels may be placed in a hot environment that causes a gel to prematurely form. After an extended period of time, the strength of such gels deteriorates to an extent that significant leakage will likely occur during use.

As such, a need currently exists for an improved vaginal treatment composition.

SUMMARY OF THE INVENTION

In accordance with one embodiment of the present invention, a vaginal treatment composition is disclosed that comprises at least anionic polysaccharide that is capable of forming a gel in the presence of vaginal mucosa. For example, the anionic polysaccharide may be a low acyl gellan gum (e.g., deacylated or nonacylated). In addition to an anionic polysaccharide, the vaginal treatment composition also comprises an effective amount of at least one therapeutic agent. In one embodiment, for instance, the therapeutic agent may be capable of inhibiting and/or killing *Gardnerella vaginalis, Candida albicans*, and/or *Trichomonas vaginalis* when exposed thereto.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which.

DETAILED DESCRIPTION OF REPRESENTATIVE EMBODIMENTS

Definitions

Figure 1:
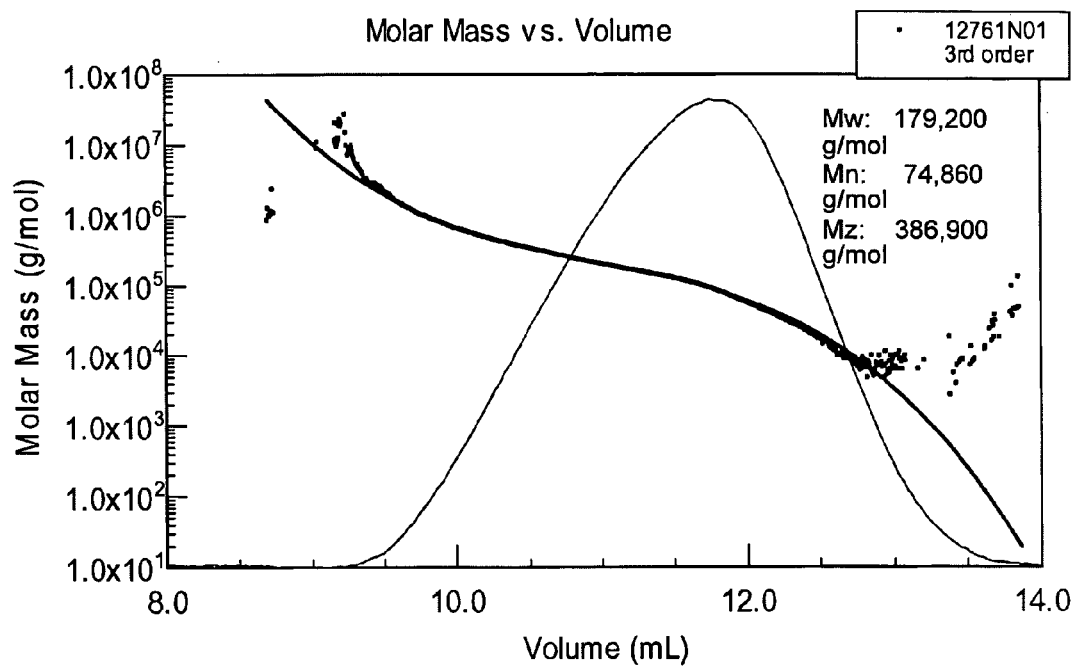
FIG. 1 is a light scattering analysis obtained in Example 4 for a solution containing only KELCOGEL®.

As used herein, the term "vagina" generally refers to the internal structure of the female reproductive tract extending from the cervix of the uterus to the vestibule. The term is also intended to include the external genitalia (e.g., labia majora, labia minora, and clitoris).

As used herein, the term "inhibit" generally means to reduce by a measurable amount or to prevent entirely.

As used herein, the term "treat" generally means to block at least one symptom that characterizes a pathologic condition in an animal threatened by or afflicted with the condition.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

The present invention is generally directed to a vaginal treatment composition that rapidly forms a gel when placed into contact with monovalent or polyvalent cations, such as sodium ($Na^+$) and calcium ($Ca^{2+}$) cations found in vaginal mucosa. The gel may form in less than about 1 hour, in some embodiments less than about 1 minute, and in some embodiments, less than about 30 seconds. Among other things, such rapid gelation reduces the likelihood of leakage during use. In addition, because the gel may form intravaginally, it is more likely to retain its structure and shape over an extended period of time. In this manner, the gel may provide the prolonged release of a therapeutic agent that inhibits and/or treats vaginal infection. For instance, the gel may remain within the vagina for about 2 to about 48 hours to provide the desired effect.

I. Vaginal Treatment Composition

A "gel" is a colloid in which a disperse phase combines with a dispersion medium to produce a jelly-like, solid or semi-solid material. Although a variety of compounds may be employed, water is usually employed as the dispersion medium for the gel to optimize biocompatibility. Other possible dispersion mediums include non-aqueous solvents, including glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Typically, the dispersion medium (e.g., water) constitutes greater than about 75 wt/vol %, in some embodiments greater than about 90 wt/vol %, and in some embodiments, from about 95 wt/vol % to about 99 wt/vol % of the vaginal treatment composition. As used herein, the designation "wt/vol %" or "wt/vol" or refers to the value obtained by dividing the weight of a substance (in grams) by the volume of the solution (in milliliters), and then multiplying by 100.

A. Anionic Polysaccharides

In the vaginal treatment composition of the present invention, the disperse phase is a three-dimensional polymer network formed by an anionic polysaccharide. Anionic polysaccharides include polysaccharides having an overall anionic charge, as well as neutral polysaccharides that contain anionic functional groups. It is well known that vaginal mucosa contains certain monovalent and polyvalent cations, such as sodium ($Na^+$) and calcium ($Ca^{2+}$) ions. See e.g., Owen, D. H. and Katz, D. F., A Vaginal Fluid Simulant, Contraception, 59, 91-95 (1999). Such cations may crosslink anionic polysaccharide molecules to form a three-dimensional network, i.e., a gel. The ability to form a gel based on the reaction with ions contained in vaginal mucosa provides a variety of benefits. For example, due to their high molecular weight, most anionic polysaccharides will not be absorbed by the body such that their gel-like properties may be maintained while in the vagina. Still another benefit of saccharide-based gels is that they are generally biocompatible and biodegradable. Further, unlike compositions in which gel formation is induced by temperature (i.e., thermogels), the vaginal treatment composition of the present invention may be stored and transported at a variety of different temperatures without fear of premature gelation. It should be understood, however, that the composition may be partially or wholly gelled prior to application to the vagina in other embodiments of the present invention.

Generally speaking, any of a variety of anionic polysaccharides capable of forming a gel when contacted with vaginal mucosa may be used in the present invention. Such gel-forming anionic polysaccharides are typically stable over the normal acidic pH values found in the vagina (e.g., from about 2.5 to about 5.5). For instance, some suitable examples of gel-forming anionic polysaccharides include natural gums, such as gellan gum and alginate gums (e.g., ammonium and alkali metal of salts of alginic acid); chitosan; carboxymethylcellulose, pectins, carrageenan, xantham gum, and derivatives or salts thereof. The particular type of anionic polysaccharide selected will depend, in part, on the nature of the vaginal treatment composition and the other components used therein. For example, carrageenan is sensitive to particular types of cations, e.g., it typically gels in the presence of potassium but not sodium. Glycuronans, likewise, typically gel in the presence of divalent cations (e.g., $Ca^{2+}$), but not monovalent cations (e.g., $Na^+$). Xanthan gum may gel in the presence of divalent cations, but only at a relatively high pH.

Although any of the above-described anionic polysaccharides may be used in the present invention, gellan gum is particularly desired for use in the present invention, either alone or in combination with other gelling agents, because it is able to form a gel in the presence of a wide variety of different cations, including both monovalent and divalent cations. Gellan gum is produced from strains of the bacteria, *Sphingomonas Elodea*. Typically, the gum is produced as an extracellular product through the aqueous cultivation of the microorganisms in a medium containing appropriate carbon, organic and inorganic nitrogen, and phosphate sources. The fermentation is carried out under sterile conditions with strict control of aeration, agitation, temperature, and pH. When fermentation is complete, the resulting viscous broth is pasteurized to kill viable cells prior to recovery of the gum. The gum may be recovered in a variety of ways. For instance, direct recovery from the broth yields the gum in its native or "high acyl" form. On the other hand, recovery after deacylation (e.g., by treatment with a base) yields the gum in its "low acyl" form. The degree of deacylation (i.e., the percentage of acyl groups removed) may be controlled by varying the temperature (e.g., 25° C. to 85° C.), the amount of base (e.g., pH>7.0), the reaction time, etc. Regardless, the constituent sugars of gellan gum are glucose, glucuronic acid and rhamnose in the molar ratio of about 2:1:1. These sugars are linked together to give a primary structure having a linear tetrasaccharide repeat unit.

As stated, the gellan gum may be either high or low acyl gellan. In the high acyl (or "native") form, two acyl substituents, acetate and glycerate, are present. Both substituents are located on the same glucose residue and, on average, there is one glycerate per repeat unit and one acetate per every two repeat units. In the low acyl form, the acyl groups may be wholly or partially removed through deacylation. The degree of deacylation of deacylated gellan gums may be at least about 20%, in some embodiments at least about 50%, and in some embodiments, at least about 75%. Alternatively, the low acyl gellan gum may simply be "nonacylated" in that it is formed without acyl groups by genetically engineered bacteria. Regardless of the manner in which they are formed, low acyl gellan gums generally have a gelation temperature within the range 30° C. to 50° C. depending on the nature and concentration of the cations present. In contrast, most high acyl gellan gums have a gelation temperature of above 50° C. For this reason, it is normally desired that a low acyl gellan gum be utilized in the present invention so that it may gel at body temperatures of about 37° C., but remain stable at typical storage and transportation temperatures of about 25° C. However, it should be understood that, in some cases, premature gelling may be acceptable or even desired. In addition, low acyl gellan gums are also firm and elastic, and thus may retain their shape after delivery to the vaginal cavity.

Of course, other types of gellan gums may also be used in the present invention. In fact, the term "gellan gum" is intended to encompass any form of gellan, including native gellan, clarified gellan, deacylated gellan, nonacylated gellan (e.g., produced from genetically engineered bacteria), clarified gellan (the polysaccharide is fully or partially removed from the bacterial debris), chemically modified gellan, etc. Various types of gellan gums and methods for forming such gums are described in U.S. Pat. Nos. 4,326,052; 4,326,053 to Kang, et al.; U.S. Pat. Nos. 4,377,636; 4,385,123; 4,563,366 to Baird, et al.; U.S. Pat. No. 5,190,927 to Chang, et al.; as well as U.S. Patent Application Publication No. 2003/0100078 to Harding, et al., all of which are incorporated herein in their entirety by reference thereto for all purposes. Gellan gums are commercially available from a variety of different sources. For example, GELRITE™ gellan gum is available from Sigma-Aldrich Chemical Co. of St. Louis, Mo., and is produced from a naturally occurring polysaccharide after deacylation and clarification. Deacylated gellan is also available from CP Kelco U.S., Inc. of Chicago, Ill. under the name KELCOGEL®.

The anionic polysaccharide(s) are generally present in the vaginal treatment composition in an amount sufficient to form a self-supporting gel upon contact with monovalent or polyvalent cations, such as found in vaginal mucosa. This amount may vary depending on a variety of factors, such as the nature of the polysaccharide(s), the conditions of intended use, the nature of other components in the vaginal treatment composition, and so forth. In most embodiments, however, the anionic polysaccharide(s) are present in an amount of from about 0.01 wt/vol % to about 10 wt/vol %, in some embodiments from about 0.05 wt/vol % to about 5 wt/vol %, and in some embodiments, from about 0.1 wt/vol % to about 1 wt/vol % of the vaginal treatment composition.

B. Therapeutic Agents

The vaginal treatment composition of the present invention generally contains a therapeutic agent that is capable of being released from the gel to provide a therapeutic benefit. Examples of therapeutic agents include, for instance, antibacterial agents, antimicrobial agents, antiparasitic agents, antibiotics, antihistamines, decongestants, antipruritics, antimetabolites, antiglaucoma agents, anti-cancer agents, antiviral agents, antifungal agents, antimycotics, anti-inflammatory agents, anti-diabetic agents, anesthetic agents, anti-depressant agents, analgesics, anti-coagulants, opthalmic agents, angiogenic factors, immunosuppressants, anti-allergic agents, spermicides, humectants and emollients, hormones, and so forth. Numerous such compounds are known to those of skill in the art and described, for example, in *The Pharmacological Basis of Therapeutics*, Hardman, Limbird, Goodman & Gilman, McGraw-Hill, New York, (1996), as well as U.S. Pat. No. 6,419,913 to Niemiec, et al.; U.S. Pat. No. 6,562,363 to Mantelle, et al.; 6,593,292 to Rothbard, et al.; U.S. Pat. No. 6,567,693 to Allen Jr.; and U.S. Pat. No. 6,645,181 to Lavi, et al., all of which are incorporated herein in their entirety by reference thereto for all purposes. One particularly useful class of therapeutic agents for vaginal applications is anti-inflammatory agents that reduce pain, swelling, stiffness, inflammation, etc. For example, nonsteroidal anti-inflammatory drugs (NSAIDs) may be utilized. Examples of NSAIDs include, but are not limited to, aspirin, ibuprofen, indomethacin, phenylbutazone, bromfenac, sulindac, nabumetone, ketorolac, mefenamic acid, and naproxen. Other suitable anti-inflammatory drugs are COX-2 inhibitors, such as celecoxib, meloxicam, rofecoxib, and flosulide. These agents inhibit the production of the COX-2 (cyclooxygenase-2) enzyme induced by pro-inflammatory stimuli in migratory cells and inflamed tissue.

In one particular embodiment of the present invention, the therapeutic agent is capable of inhibiting and/or treating vaginal infection. More specifically, the treatment composition may contain a therapeutic agent that is capable of inhibiting and/or killing *Gardnerella* (e.g., *Gardnerella vaginalis*), *Candida* (e.g., *Candida albicans*), and/or *Trichomonas* (e.g., *Trichomonas vaginalis*) pathogens. Desirably, such antimicrobial efficacy is achieved without substantially inhibiting the growth of *Lactobacillus acidophilus*. In this regard, the present inventors have discovered that certain sugar derivatives exhibit the desired selective inhibition and/or treatment of vaginal infection. For example, sugar alcohols are one particularly suitable class of sugar derivatives that may be used in the present invention. Sugar alcohols, also known as polyols or polyhydric alcohols, are hydrogenated forms of sugars that may be modified into compounds that retain the basic configuration of saccharides, but with different functional groups. Suitable sugar alcohols may include pentose alcohols (e.g., D-xylitol, D-arabitol, meso-ribitol (adonitol), and isomers thereof) and hexose alcohols (e.g., glycerol, meso-galacitol (dulcitol), inositol, D-mannitol, D-sorbitol, and isomers thereof). Pentose alcohols, for instance, have the same linear structure as pentoses, but are modified with one on or more alcohol groups. As an example, the Fischer open chain structures of D-xylitol, D-arabitol, and adonitol are set forth below:

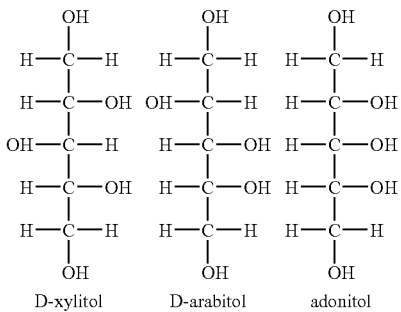

In one particular embodiment, the vaginal treatment composition employs D-xylitol as the therapeutic agent. Exogenous xylitol is metabolized to glucose and glucogen or pyruvate and lactate in the liver. Nevertheless, many bacteria are unable to utilize xylitol as an energy source, and as such, its presence may be harmful to some bacteria despite the availability of an alternative energy source, such as glucose. For instance, it is known that xylitol may reduce the growth of *Streptococcus mutans, Streptococcus salivarius, Streptococcus sanguis, Lactobacillus casei* and some strains of *Escherichia coli, Saccharomyces cerevisae* and *Salmonella typhii*. Although the anti-microbiological mechanism of xylitol is not fully understood, the present inventors believe that xylitol may be transported into a pathogen to disrupt its metabolic process and/or gene expression capabilities. For instance, xylitol may be phosphorylated through the constitutive fructose phosphotransferase system that regulates many metabolic processes and gene expression in bacteria. In addition, because bacteria adhere to host cells through carbohydrate-binding proteins, extracellular xylitol may also disturb the binding process by acting as a receptor analogue for the host cell, which could result in decreased adherence.

Still other sugar derivatives that may be used in the present invention are sugar-based polymers. For example, pentose-based polymers may be employed that contain D-fructose linked by β bonds and an α-linked D-glucose located at the terminal end of the molecule. The degree of polymerization of such polymers generally ranges from about 2 about 60. The polymers are designated as "oligofructose" when the degree of polymerization is less than about 20 and as "inulin" when it is greater than or equal to about 20. In addition, sugar-based surfactants may also be used in the present invention. For instance, one particularly effective class of sugar-based surfactants is alkyl glycosides. Alkyl glycosides are broadly defined as condensation products of long chain alcohols (e.g., $C_{8-30}$ alcohols) and a saccharide. Examples of long chain alcohols from which the alkyl group may include, but are not limited to, decyl alcohol, cetyl alcohol, stearyl alcohol, lauryl alcohol, myristyl alcohol, oleyl alcohol, and so forth. Alkyl glycosides are generally represented by the following formula:

$$(Z)_n\text{—O—R}$$

wherein,
Z is a saccharide residue;
n is from about 1 to about 1000; and
R is an alkyl group having 8 to 30 carbon atoms.

The "Z" saccharide residue of the alkyl glycoside typically has at least 3 carbon atoms, and in some embodiments, from about 3 to about 20 carbon atoms, and in some embodiments from about 5 to about 6 carbon atoms. The saccharide residue may, for instance, be a residue of glucose, fructose, maltose, maltotriose, lactose, galactose, mannose, dextrose, xylose, sucrose, leucrose, and so forth. The designation "n" represents the average number of saccharide residues in a particular sample of alkyl polyglycoside. For example, the alkyl glycoside may be a monosaccharide (n=1), disaccharide (n=2), trisaccharide (n=3), oligosaccharide (n=4 to 20), or polysaccharide (n>20). In most embodiments, "n" is greater than about 2, in some embodiments from about 2 to about 6, and in some embodiments, from about 2 to about 4. The "alkyl group" of the alkyl glycosides is generally a linear alkyl group (i.e., a straight chain alcohol residue), which typically has an even number of carbon atoms. The alkyl glycosides desirably include alkyl groups having 8 to 20 carbon atoms, in some embodiments 8 to 14, and in some embodiments, 9 to 12. One particular example of a suitable alkyl glycoside is a mixture of alkyl glycoside molecules with alkyl chains having 8 to 10 carbon atoms.

The alkyl glycoside may include a single type of alkyl glycoside molecule or a mixture of different alkyl glycoside molecules. The different alkyl glycoside molecules may be isomeric and/or may be alkyl glycoside molecules with differing alkyl groups and/or saccharide residues. Alkyl glycoside isomers are alkyl polyglycosides which, although including the same alkyl ether residues, may vary with respect to the location of the alkyl ether residue in the alkyl glycoside, as well as isomers which differ with respect to the orientation of the functional groups about one or more chiral centers in the molecules. For example, an alkyl glycoside may include a mixture of molecules with saccharide residues that are mono-, di- or oligosaccharides derived from more than one 6 carbon saccharide residue and in which the mono-, di- or oligosaccharide has been etherified by reaction with a mixture of fatty alcohols of varying carbon chain length. When more than one saccharide residue is present on average per alkyl glycoside molecule (i.e., "n" is greater than 1), the individual saccharide subunits within the same molecule may be identical or different. When the individual subunits are not all identical, the order and distribution of subunits is typically random.

Alkyl glycosides may be produced using well-known techniques. Alkyl mono and polyglycosides are generally prepared by reacting a monosaccharide, or a compound hydrolyzable to a monosaccharide, with an alcohol such as a fatty alcohol in an acid medium. For example, U.S. Pat. Nos. 5,527,892 and 5,770,543, which are incorporated herein in their entirety by reference thereto for all purposes, describe alkyl glycosides and/or methods for their preparation. Commercially available examples of suitable alkyl glycosides include Glucopon™ 220, 225, 425, 600 and 625, all of which are available from Cognis Corp. of Cincinnati, Ohio. These products are mixtures of alkyl mono- and oligoglucopyranosides with alkyl groups based on fatty alcohols derived from coconut and/or palm kernel oil. Glucopon™ 220, 225 and 425 are examples of particularly suitable alkyl polyglycosides. Glucopon™ 220 is an alkyl polyglycoside that contains an average of 1.4 glucosyl residues per molecule and a mixture of 8 and 10 carbon alkyl groups (average carbons per alkyl chain-9.1). Glucopon™ 225 is a related alkyl polyglycoside with linear alkyl groups having 8 or 10 carbon atoms (average alkyl chain-9.1 carbon atoms) in the alkyl chain. Glucopon™ 425 includes a mixture of alkyl polyglycosides that individually include an alkyl group with 8, 10, 12, 14 or 16 carbon atoms (average alkyl chain-10.3 carbon atoms). Glucopon™ 600 includes a mixture of alkyl polyglycosides that individually include an alkyl group with 12, 14 or 16 carbon atoms (average alkyl chain 12.8 carbon atoms). Glucopon™ 625 includes a mixture of alkyl polyglycosides that individually include an alkyl group having 12, 14 or 18 carbon atoms (average alkyl chain 12.8 carbon atoms). Still other suitable alkyl glycosides are available from Dow Chemical Co. of Midland, Mich. under the Triton™ designation, e.g., Triton™ CG-110 and BG-10.

Besides alkyl glycosides, another suitable class of sugar-based surfactants is saccharide fatty acid esters, which generally have the following formula:

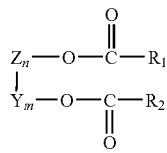

wherein,
Z is a saccharide residue or alcohol thereof;
Y is a saccharide residue or alcohol thereof;
m is from about 1 to about 1000;
n is from about 1 to about 1000;
$R_1$ is an alkyl group having 8 to 30 carbon atoms; and
$R_2$ is an alkyl group having 8 to 30 carbon atoms.

In addition, still another suitable class of sugar-based nonionic surfactants is glucosamides, which generally have the following formula:

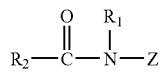

wherein,
Z is a polhydroxyhydrocarbyl moiety having a linear hydrocarbyl chain with a least 3 hydroxyls directly connected to the chain, or an alkoxylated derivative (preferably ethoxylated or propoxylated) thereof;
n is from about 1 to about 1000;
$R_1$ is H, $C_1$-$C_4$ alkyl, 2-hydroxyethyl, 2-hydroxy-propyl, preferably about $C_1$-$C_4$ alkyl, more preferably methyl or ethyl, most preferably methyl; and
$R_2$ is $C_5$-$C_{31}$ alkyl or alkenyl, preferably about $C_7$-$C_{19}$ alkyl or alkenyl, more preferably about $C_9$-$C_{17}$ alkyl or alkenyl, most preferably about $C_{11}$-$C_{15}$ alkyl or alkenyl. An especially preferred surfactant corresponding to the above structure is coconut alkyl N-methyl glucoside amide (i.e., wherein the $R_1$CO— moiety is derived from coconut oil fatty acids).

Besides sugar derivatives, certain types of sugars are also believed to provide the desired selective inhibition and/or treatment of vaginal infection. For instance, pentoses (e.g., five carbon-based sugars) having the general structure, $C_5H_{10}O_5$, may be used in some embodiments of the present invention. Exemplary pentoses include D-ribose, D-ribulose, D-arabinose, D-xylose, D-xylulose, and D-lyxose, and isomers thereof. As an example, the structures of D-ribose, D-xylose, D-lyxose, and D-arabinose are set forth below:

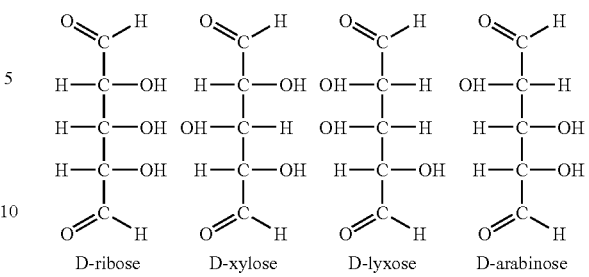

Of course, other sugars, such as hexoses (e.g., D-dulcitose, D-inositose, D-mannitose, and isomers thereof) may also be used in the present invention. Although sugars and sugar-based compounds are effective in inhibiting and/or treating vaginal infection, it should be understood that any compound that exhibits the desired antimicrobial efficacy may be used in the present invention. For example, another class of suitable therapeutic agents may include phenolic acids. Suitable phenolic acids may include, for instance, p-hydrobenzoic acid, protocatechuic acid, vanillic acid, chlorogenic acid, caffeic acid, ferulic acid, gallic acid, sinapic acid, syringic acid, coumaric acid, cinnamic acid, gentisic acid, saliclic acid, veratric acid, anisic acid, crotonic acid, hydroxy benzoic acid, hydroxy phenyl acetic acids, and derivatives and isomers thereof.

The therapeutic agent is placed into contact with a vagina in an effective amount to achieve the desired therapeutic benefit. When used to inhibit and/or treat vaginal infection, for example, an "effective amount" of a therapeutic agent is an amount sufficient to inactivate, but not necessarily kill, pathogenic microorganisms responsible for vaginal infection. In fact, although not required, it may be desired to use a concentration that does not significantly affect or inhibit the growth characteristics of the normal vaginal flora or otherwise significantly irritate the vaginal tissue when used at inhibitory, noncytotoxic, or clinical concentrations. For example, the therapeutic agent(s) are desirably employed at a concentration of about 0.01 wt/vol % to about 20 wt/vol %, in some embodiments from about 0.1 wt/vol % to about 10 wt/vol %, in some embodiments from about 0.2 wt/vol % to about 5 wt/vol %, and in some embodiments from about 0.5 wt/vol % to about 4.5 wt/vol %. It should be understood, however, that the dosage may vary with the age, condition, and type of infection suffered by the patient, and may be readily determined by one of skill in the art.

C. Preservatives

The vaginal treatment composition may also contain a preservative or preservative system to inhibit the growth of microorganisms over an extended period of time. Suitable preservatives for use in the present compositions may include, for instance, alkanols, disodium EDTA (ethylenediamine tetraacetate), EDTA salts, EDTA fatty acid conjugates, isothiazolinone, benzoic esters (parabens) (e.g., methylparaben, propylparaben, butylparaben, ethylparaben, isopropylparaben, isobutylparaben, benzylparaben, sodium methylparaben, and sodium propylparaben), benzoic acid, propylene glycols, sorbates, urea derivatives (e.g., diazolindinyl urea), and so forth. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate). Another suitable preservative is Kathon CG®, which is a mixture of methylchloroisothiazolinone and methylisothiazolinone available from Rohm & Haas; Mackstat H 66 (available from Mcintyre Group, Chicago, Ill.). Still another suitable preservative system is a combination of 56% propylene glycol, 30% diazolidinyl urea, 11% methylparaben, and 3% propylparaben available under the name GERMABEN® II from International Specialty Products of Wayne, N.J. In one particular embodiment of the present invention, benzoic acid is employed as a preservative due to its broad efficacy against a wide variety of organisms, lack of odor, and optimal performance at the low pH values often employed for the vaginal treatment composition (e.g., from about 2.5 to about 5.5).

When utilized, the amount of the preservative or preservative system utilized in the vaginal treatment composition may generally vary depending on the relative amounts of the other components present within the composition. For example, in some embodiments, preservative(s) are present in the composition in an amount from about 0.001 wt/vol % to about 5 wt/vol %, in some embodiments from about 0.001 wt/vol % to about 1 wt/vol %, and in some embodiments, from about 0.1 wt/vol % to about 0.15 wt/vol % of the composition.

D. Tonicity Agents

To avoid adverse physiological effects, the vaginal treatment composition is generally "isotonic" in that it has an osmolarity that is substantially similar to vaginal mucosa (i.e., about 290 milliosmoles per liter ("mOsm/L")). For example, an isotonic vaginal treatment composition may have an osmolarity of from about 270 to about 310 mOsm/L, in some embodiments from about 280 to about 300 mOsm/L, and in one embodiment, about 290 mOsm/L. The osmolarity of the vaginal treatment composition may be estimated using the following equation:

$$O_{composition} = \Sigma O_{species}$$

wherein, $O_{species}$ is the osmolarity of a species in the composition. The osmolarity of a particular species is likewise determined using the following equation:

$$O_{species} = [c/m] \times n \times \phi \times 1000$$

wherein, c is the concentration of the species, in grams per liter;

m is the average molecular weight of the species;

n is the number of particles that dissociate from the molecule;

$\phi$ is the osmotic coefficient of the species.

If desired, a tonicity agent may be employed in the vaginal treatment composition to help achieve such an osmolarity. Conventionally, ionic salts, such as sodium chloride, potassium chloride, and calcium chloride, were often used to correct and balance the osmolarity of mucosal compositions. Because the vaginal treatment composition of the present invention employs an ion-responsive polysaccharide, however, such ionic salts may promote premature gelation. In most cases, the vaginal treatment composition is actually substantially free from monovalent and/or divalent cations that would cause premature gelation. Thus, nonionic tonicity agents are desired in most embodiments of the present invention. Examples of such nonionic tonicity agents may include, for instance, dextrose, glycerin, propylene glycol, mannitol, sorbitol, xylitol, trehalose, sucrose, etc. It should be understood, however, that ionic salts may be employed in some embodiments of the present invention.

When utilized, any effective amount of the tonicity agent(s) may be employed in the vaginal treatment composition to achieve the desired osmolarity. For example, the tonicity agent(s) are typically present in an amount from about 0.01 wt/vol % to about 5 wt/vol %, in some embodiments from about 0.05 wt/vol % to about 2 wt/vol %, and in some embodiments, from about 0.1 wt/vol % to about 1 wt/vol % of the vaginal treatment composition. One particularly beneficial aspect of the present invention, however is that the above-described sugar or sugar-based therapeutic agents may provide the desired osmolarity without the need for additional tonicity agents. For example, xylitol may be particularly effective in achieving both the desired osmolarity and the desired biological activity. Such dual functionality provides a variety of benefits to the resulting composition, including the elimination of unnecessary components that would otherwise increase production complexity and costs.

E. pH Modifiers

As noted above, the anionic polysaccharide of the vaginal treatment composition is capable of gelling in the presence of cations, such as those found naturally in vaginal mucosa. In some cases, however, it may be desirable to enhance the gelation rate during use to reduce the likelihood of leakage just after insertion of the composition into the vagina. In this regard, the present inventors have discovered that compositions with lower pH values generally gel at a faster rate. In addition, gels formed from such low pH compositions also tend to have enhanced strength. Of course, too low of a pH value may be irritating and disruptive to the mildly acidic vaginal environment. Thus, to balance gel performance and biocompatibility, the pH of the vaginal treatment composition is typically maintained within a range of from about 2.5 to about 5.5, in some embodiments from about 2.5 to about 5.0, and in some embodiments, from about 3.0 to about 4.5.

If desired, various pH modifiers may be utilized in the vaginal treatment composition to achieve the desired pH level. Some examples of pH modifiers that may be used in the present invention include, but are not limited to, mineral acids, sulfonic acids (e.g., 2-[N-morpholino] ethane sulfonic acid), carboxylic acids, and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, acetic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid. Basic pH modifiers may also be used in some embodiments of the present invention to provide a higher pH value. Suitable pH modifiers may include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine.

Apart from simply providing the desired pH level, the present inventors have discovered that certain pH modifiers may also synergistically improve the inhibition and/or treatment of vaginal infection when used in combination with a therapeutic agent. As described above, for instance, a phenolic acid may be employed that imparts both the desired antimicrobial efficacy and pH level to the vaginal treatment composition. For example, the present inventors have discovered that gallic acid (i.e., trihydroxybenzoic acid) is particularly effective in inhibiting the growth of *Gardnerella vaginalis*, as well as imparting a pH level of between about 3.0 to about 4.5 to the vaginal treatment composition.

When utilized, the pH modifier may be present in any effective amount needed to achieve the desired pH level. In some embodiments, the pH modifier(s) are present in an amount between about 0.001 wt/vol % to about 5 wt/vol %, in some embodiments between about 0.005 wt/vol % to about 1 wt/vol %, and in some embodiments, between about 0.01 wt/vol % to about 0.25 wt/vol % of the vaginal treatment composition.

II. Intravaginal Administration

Because the vaginal treatment composition is topically administered to the vagina prior to gelation, it may generally be provided in any desired form (e.g., liquid, powder, etc.). In fact, one particular benefit of the present invention is that the composition may be administered as a liquid, which allows for the selection of a wider variety of administration techniques than would otherwise be available for a solid or semi-solid gel. For example, one technique that may be employed includes dispensing the composition through a liquid applicator, such as a syringe or tube, into the vaginal cavity. The administered volume of the composition may constitute a single dose or two or more doses. Although not necessarily required, the vaginal treatment composition of the present invention may also be sterilized prior to administration. Sterilization may be accomplished by any technique known in the art, such as using a gas (e.g., ethylene oxide), radiation (e.g., gamma), or heat (autoclaving). If desired, the composition may be subjected to one or more filtration steps prior to sterilization to help remove contaminants.

The present invention may be better understood with reference to the following examples.

Microorganisms and Culture Media

*Gardnerella vaginalis* was obtained from the American Type Culture Collection (ATCC #14018). The culture medium was Casman's medium base (BD 229010) with 5% rabbit blood (ATCC medium 70).

*Trichomonas vaginalis* was obtained from the American Type Culture Collection (ATCC #30001). The culture medium was LYI-S-2 medium (ATCC medium 2154).

*Candida albicans* was obtained from the American Type Culture Collection (ATCC), catalog number 96113. The culture medium was YM medium (ATCC medium 200).

*Lactobacillus acidophilus* was obtained from the American Type Culture Collection (ATCC #4356). The culture medium was *Lactobacilli* MRS broth (ATCC medium 416).

EXAMPLE 1

Vaginal treatment composition samples were formed from a gellan gum obtained from CP Kelco U.S., Inc. of Chicago, Ill. under the name KELCOGEL®. The samples contained varying amounts of the KELCOGEL® gum (i.e., 0.1%, 0.2%, 0.3%, 0.4%, 0.5%, 0.6%, and 0.7% (wt/vol)) and were formed by dissolving the powder in deionized water heated to 75° C. After cooling to room temperature, 500 microliter-aliquots of the solutions were added to glass vials. After heating to body temperature (i.e., 37° C.), "SVF" was then added to the glass vials. "SVF" refers to simulated vaginal fluid and was prepared according to the recipe outlined in Owen, D. H. and Katz, D. F., A Vaginal Fluid Simulant, *Contraception*, 59, 91-95 (1999). The volume of SVF added varied from 50 microliters to 500 microliters, at 50-microliter increments.

The gelation and thickening properties of each sample was observed initially and after 24 hours. The addition of SVF to the 0.1%, 0.2%, and 0.3% (wt/vol) KELCOGEL® samples led to thickening, but not complete gelation, at and above 200 microliters of SVF. For the 0.1% (wt/vol) KELCOGEL® samples, the addition of 450 and 500 microliters of SVF led to thickening within about 20 seconds. The thickening time was reduced to about 10 seconds for the 0.2% (wt/vol) and 0.3% KELCOGEL® samples. It was also observed that the KELCOGEL® samples started to form self-supporting gels at concentrations of 0.4% (wt/vol) and higher, with the most desirable gel properties achieved at approximately 0.7% (wt/vol). However, increasing amounts of SVF above about 300 microliters appeared to reduce gelation.

EXAMPLE 2

A first solution of 0.4% (wt/vol) KELCOGEL® and 150 microliters of SVF was prepared as described in Example 1. A self-supporting gel immediately formed, and was then incubated overnight at 37° C. in a water bath. In addition, a second solution was prepared in a glass vial and immediately incubated overnight at 37° C. prior to forming a gel. The following day, both glass vials were removed from the water bath. The gel formed from the first solution exhibited no signs of viscosity decrease or gel breakdown after incubation. Additionally, the second solution was also observed to have formed a self-supporting gel after incubation, thereby suggesting that body temperature did not negatively impact the ability of the solution to form a gel.

EXAMPLE 3

Solutions were formed from xylitol and a gellan gum obtained from CP Kelco U.S., Inc. of Chicago, Ill. under the name KELCOGEL®. The solutions contained 0.7% (wt/vol) of the KELCOGEL® gum and 4.4% (wt/vol) xylitol, and were formed by dissolving 0.07 grams of the polymer powder and 0.44 grams of xylitol into 10 milliliters of water at a temperature between 70° C. to 80° C. After vortexing the solutions to help dissolve the solids, they were allowed to cool to room temperature. After cooling, the pH of the solutions was adjusted using varying amounts of either acetic acid or lactic acid.

The osmolarity of the solutions was estimated using the following equation:

$$O_{composition} = \Sigma O_{species}$$

wherein, $O_{species}$ is the osmolarity of a species in the composition. The osmolarity of a particular species is likewise determined using the following equation:

$$O_{species} = [c/m] \times n \times \phi \times 1000$$

wherein, c is the concentration of the species, in grams per liter;

m is the average molecular weight of the species;

n is the number of particles that dissociate from the molecule;

$\phi$ is the osmotic coefficient of the species.

More specifically, the molecular weight of the KELCOGEL® gellan gum was approximately 500,000 grams per mole. Because gellan gum does not generally dissociate, it was considered to have an n value equal to 1. Xylitol has a molecular weight of 154.12 grams per mole and was also considered to have an n value equal to 1 due to its lack of dissociation. Lactic acid and acetic acid have molecular weights of 90.08 and 122.12 grams per mole, respectively. In addition, lactic acid and acetic acid dissociate into two (2) species (though not necessarily to completion), and thus were considered to have an n value equal to 2. With respect to the osmotic coefficient $\phi$, it is well known that its value depends on its concentration and chemical properties of the particular molecule. Generally speaking, the value of $\phi$ for a solute approaches 1 as it becomes more dilute in solution. Thus, due to the low concentrations of KELCOGEL® gellan gum, xylitol, lactic acid, and acetic acid employed in the vaginal treatment composition, it was assumed that the value of $\phi$ was 1 for each species. From the above, it was determined that the solutions were isotonic, e.g., between about 270 to about 310 mOsm/L. The properties of the solutions are set forth below in Tables 1 and 2.

TABLE 1

Acetic Acid-Modified Compositions

| Sample | Gum (wt/vol %) | Xylitol (wt/vol %) | Acetic Acid (microliters) | pH | Properties |
|---|---|---|---|---|---|
| 1 | 0.7 | — | 10 (pure) | 3.0 | Gelled rapidly |
| 2 | 0.7 | — | 10 (1:100 dilution) | 4.8 | Thickened, but did not gel |
| 3 | 0.7 | 4.4 | 50 (1:100 dilution) | 4.5 | Thickened, but did not gel |
| 4 | 0.7 | 4.4 | 240 (1:100 dilution) | 4.0 | Very loose gel (after 24 hours) |
| 5 | 0.7 | 4.4 | 1700 (1:100 dilution) | 3.6 | Very loose gel (after 24 hours) |
| 6 | 0.7 | 4.4 | 4000 (1:100 dilution) | 3.4 | Self-supporting gel after ~20 minutes |

TABLE 2

Lactic Acid-Modified Compositions

| Sample | Gum (wt/vol %) | Xylitol (wt/vol %) | Lactic Acid (microliters) | pH | Properties |
|---|---|---|---|---|---|
| 7 | 0.7 | — | 50 (pure) | 3.0 | Immediately formed strong gel |
| 8 | 0.7 | — | 10 (pure) | 3.7 | Gelled |
| 9 | 0.7 | — | 10 (1:100 dilution) | 5.4 | — |
| 10 | 0.7 | — | 20 (1:100 dilution) | 4.6 | Thickened, but did not gel |
| 11 | 0.7 | 4.4 | 25 (1:100 dilution) | 4.7 | Thickened, but did not gel |
| 12 | 0.7 | 4.4 | 40 (1:100 dilution) | 4.5 | Thickened, but did not gel (after 24 h.) |
| 13 | 0.7 | 4.4 | 120 (1:100 dilution) | 4.0 | Very loose gel (after 24 hours) |
| 14 | 0.7 | 4.4 | 540 (1:100 dilution) and 12 (pure) | 3.5; 3.4 | Self-supporting gel (after 24 hours) |
| 15 | 0.7 | 4.4 | 15 (pure) | 3.3 | Gelled rapidly (self-supporting in a few minutes) |
| 16 | 0.7 | 4.4 | 40 (1:100 dilution) | 4.5 | Thickened, but did not gel |

As indicated, xylitol did not appear to negatively impact the gelation ability of the polymer, nor did it appear to affect the gelation time. Further, the solutions of lower pH typically formed self-supporting gels slightly faster, but all solutions appeared to form self-supporting gels in the vials within one minute. An interesting discovery during initial experimentation with the pH modifiers was that a very small amount of highly concentrated or pure acid rapidly and completely gelled the solution. Thus, the strength of the gel may be tunable via adjustment of acid strength and concentration.

EXAMPLE 4

The ability to sterilize the vaginal treatment composition was demonstrated. Nine solutions were initially formed as set forth below in Table 3.

TABLE 3

Composition of Solutions

| Sample | Gum (wt/vol %) | Xylitol (wt/vol %) | Starting pH | Acetic Acid (microliters, 1:100 dilution) | Ending pH |
|---|---|---|---|---|---|
| 1 | 0.7 | 4.4 | 5.2 | 240 | 4.1 |
| 2 | 0.7 | 4.4 | 5.1 | 280 | 4.1 |
| 3 | 0.7 | 4.4 | 5.3 | — | 5.3 |
| 4 | 0.7 | — | 5.9 | 240 | 4.1 |
| 5 | 0.7 | — | 5.8 | 280 | 4.1 |
| 6 | 0.7 | — | 5.9 | — | 5.9 |
| 7 | — | 4.4 | 5.3 | 240 | 3.9 |
| 8 | — | 4.4 | 5.2 | 240 | 3.8 |
| 9 | — | 4.4 | 5.4 | — | 5.4 |

One pH-modified and one non-modified sample were then autoclaved in a liquid cycle for 20 minutes. After autoclaving, the solutions appeared to undergo a reduction in viscosity. As this could have been a result of the intense heat, the solutions were cooled and observed 72 hours later for comparison to un-autoclaved counterparts. The un-autoclaved samples-formed very loose gels over the 72-hour period, while the autoclaved solutions remained ungelled. To ensure that the extreme heat of the autoclave did not alter the pH of the solutions (e.g., through volatilization of acetic acid), the pH of each solution was determined in a laminar flow hood using colorpHast® pH indicator strips (available from EMD Chemicals, Inc.). All solutions maintained their pre-autoclave pH values. After checking that the pH remained unchanged in the autoclaving process, 500 microliters of each solution was mixed with 150 microliters of SVF and the gelation behavior was observed.

Figure 2:
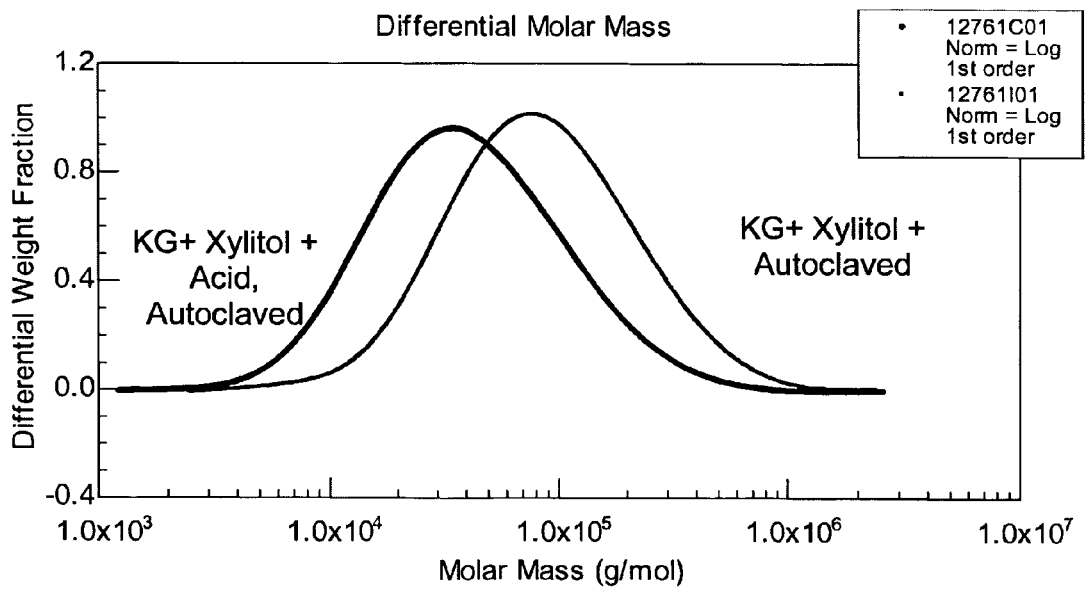
FIG. 2 is an overlay plot of Differential Molar Mass obtained in Example 4 for samples containing KELCOGEL® and xylitol, with and without acetic acid.
Figure 3:
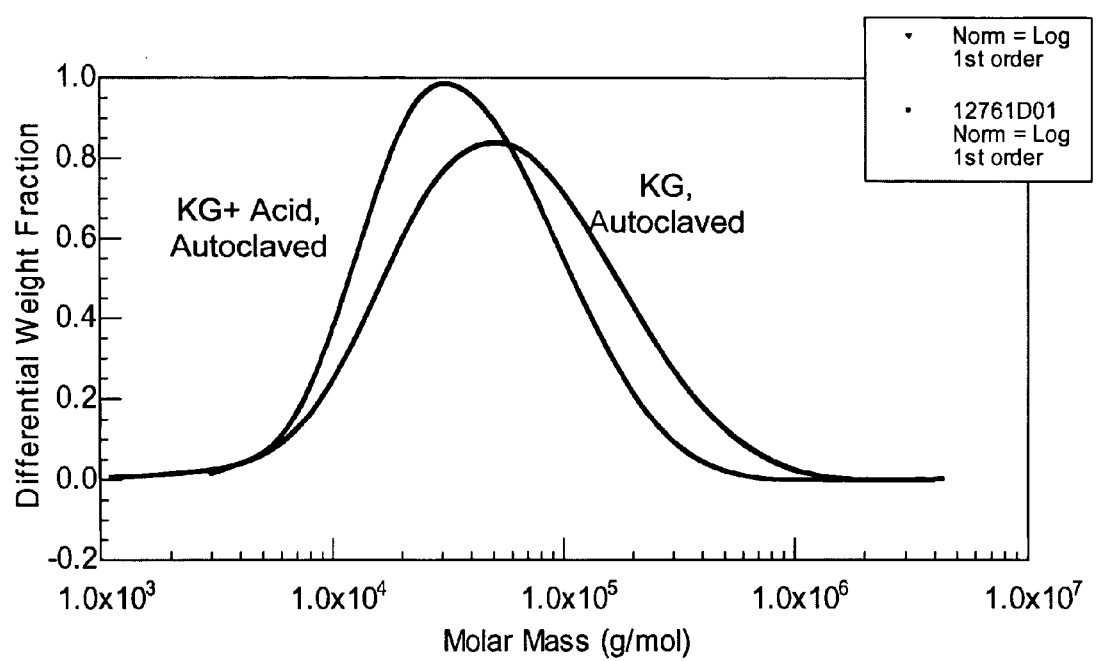
FIG. 3 is an overlay plot of Differential Molar Mass obtained in Example 4 for samples containing KELCOGEL®, with and without acetic acid.

Upon analysis, it was determined that only the solutions that were pH-modified and then autoclaved did not form gels. In addition, the solutions that were not pH modified were observed to exhibit the same behavior as the un-autoclaved, pH-modified control. This suggested that the reason for the change in gelation behavior was somehow related to the effect of heat and acid on the polymer. Although certainly not intending to be limited by theory, one possibility was that the heated acid cut the polymer chains, resulting in a chain length that was too small to form the physical entanglements needed for ion-induced gelation. To test this theory, Samples 1, 3, 4, 6, 7, and 9 were subjected to light scattering molecular weight analysis. The results are set forth in FIGS. 1-3. In particular, FIG. 1 provides the spectra for KELCOGEL®, while FIGS. 2-3 illustrate the molecular weight differences between Samples 1 and 3 (FIG. 2) and Samples 4 and 6 (FIG. 3). The analysis revealed a decrease in molecular weight of the KELCOGEL® polymer when the acid was present during autoclaving.

EXAMPLE 5

A solution was formed from 0.07 grams KELCOGEL®, 0.44 grams xylitol, and 0.0075 grams gallic acid by adding 10 milliliters of hot water (70 to 80° C.) to the powders and vortexing to dissolve. When cooled, the pH was measured and found to be about 4.0. 500 microliters of this solution was then reacted with 150 microliters of SVF and monitored for gelation behavior. The solution was also autoclaved and the gel test with SVF repeated. Upon analysis, the gallic-acid containing solution was observed to exhibit a low viscosity and a gelation rate in a glass vial of 10 seconds. After autoclaving, however, the solution did not gel with SVF.

EXAMPLE 6

The ability of the vaginal treatment composition of the present invention to inhibit and/or treat vaginal infection was demonstrated. Initially, eight (8) solutions were formed as set forth below in Table 4.

TABLE 4

Solution Composition

| Sample | KELCOGEL ® (wt/vol %) | Xylitol (wt/vol %) | Gallic Acid (wt/vol %) | pH |
|---|---|---|---|---|
| Control | — | — | — | 6 |
| 1 | 0.7 | — | — | 6 |
| 2 | 0.7 | 4.4 | — | 6 |
| 3 | 0.7 | 4.4 | 0.075 | 4 |
| 4 | 0.7 | — | 0.075 | 4 |
| 5 | — | 4.4 (in water) | — | 6 |
| 6 | — | — | 0.075 | 4 |
| 7 | — | 4.4 (in growth medium) | — | 6 |

Samples 1-2 were prepared by dissolving the KELCOGEL® (0.07 grams) and/or xylitol (0.44 grams) into 10 milliliters of water heated to between 70° C. to 80° C. Samples 3-4 and 6 were formed by first autoclaving a gallic acid stock solution (0.75 grams of gallic acid/20 mL water), autoclaving, and then adding 200 microliters of sterile gallic acid (0.0075 grams) to each sterile solution. Sample 5 was formed by dissolving 0.44 grams of xylitol in deionized water, followed by autoclaving. Sample 7 was formed by dissolving 0.44 grams of xylitol in sterilized growth medium for *Gardnerella vaginalis* and then filtering. The amount of xylitol was selected to yield isotonic solutions. After vortexing the solutions to help dissolve the solids, they were allowed to cool to room temperature.

Upon formation, 1 milliliter of each control or sample solution was then added into a culture tube, followed by the addition of 0.8 milliliters of growth medium for *Gardnerella vaginalis*. To this mixture was added 0.2 milliliters of a *Gardnerella vaginalis* suspension (at a concentration of around $10^6$ cfu/ml; diluted from $10^8$ cfu/ml stock). The tubes were incubated in culture tubes at 37° C. After 24 and 48 hours, the optical density was measured for each sample at wavelengths of 450 and 595 nanometers. The 24-hr solution samples were then diluted at 0.001× and 0.0001×. 3 milliliters of growth medium were then added into the 24-hour composition samples, followed by 1 hour of shaking at 30° C. Solution was then taken from well-shaken test tubes and diluted at 0.001× and 0.0001×. "WASP" (Whitely Automatic Spiral Plate) spiral plating equipment from Don Whitely Scientific Limited was used to plate 100 microliters of the above solutions onto agar plates. The plates were incubated overnight at 35° C. The number of colonies on each plate was counted using Proto-Col® software from Synbiosis of Frederick, Md. All samples were plated in triplicate. The results are shown in Table 5.

TABLE 5

Average Plate Counts

| Sample | Average Plate Count | St. Dev. |
|---|---|---|
| Growth media control | $1.81 \times 10^8$ | $6.36 \times 10^6$ |
| Kelcogel ® | $1.37 \times 10^8$ | $3.82 \times 10^7$ |
| Kelcogel ® + xylitol | $5.91 \times 10^5$ | $4.95 \times 10^4$ |
| Kelcogel ® + xylitol + gallic acid | $2.01 \times 10^5$ | $2.12 \times 10^4$ |
| Kelcogel ® + gallic acid | $4.14 \times 10^7$ | $4.03 \times 10^6$ |
| Xylitol | $1.56 \times 10^4$ | $5.66 \times 10^2$ |
| Gallic acid | $3.43 \times 10^4$ | $2.12 \times 10^3$ |
| Xylitol in growth media | $2.40 \times 10^4$ | $2.83 \times 10^3$ |

As indicated, the presence of KELCOGEL® did not significantly inhibit or increase the growth of *Gardnerella vaginalis*. On the other hand, xylitol exhibited significant inhibition for *Gardnerella vaginalis* growth, both in solutions (growth medium and D.I water) and in the KELCOGEL® compositions. Further, the solution containing both xylitol and gallic acid exhibited even better inhibition for *Gardnerella vaginalis* growth than the solution containing only xylitol. It should also be noted that the inhibition of *Gardnerella vaginalis* growth, though very effective, appeared to be less for the KELCOGEL®-based solutions than for the compounds in growth media or water. This was most likely due to the fact that the therapeutic agent needed to first diffuse from the gel before contacting the bacteria.

EXAMPLE 7

The ability to form a vaginal treatment composition with a preservative was demonstrated. Initially, a solution was formed that contains 0.7% KELCOGEL®, 4.4% (wt/vol) xylitol, and 0.1% (wt/vol) benzoic acid by measuring out the appropriate powders and adding hot water (approx. 70° C.). After the solution had cooled to room temperature, the pH was adjusted to approximately 4.0 using a 1:50 solution of lactic acid so that its final concentration in solution was 0.1% (wt/vol). A larger batch (300 milliliters) was also created by adding hot water to ingredients using a high shear mixer. The 1:50 lactic acid was again added to bring the final concentration in solution to 0.1% (wt/vol). Solutions were mixed with SVF. It was observed that both the small and large-batch solutions formed self-supporting gels within 1 minute of contact with SVF.

EXAMPLE 8

A microorganism culture of $10^5$ cfu (colony forming units)/ml in a 1× phosphate buffered saline (PBS) solution (diluted from 10×PBS LIQUID CONCENTRATE from VWR Cat. No. EM-6507] was used. One milliliter of the solution was plated on proper agar plates, depending on which microorganism was being tested. The agar plates were incubated at 35° C. for 4 hours. Three 4-millimeter diameter wells were then punched in each agar plate. A test sample of 100 microliters of 5% xylitol in sterilized 2-N-morpholino ethane sulfonic buffer (0.1 M 2-[morpholino]-ethanesulfonic acid, 0.9% NaCl, pH 4.7, prepared from BupH™ MES Buffer Saline Pack from Cat. No. 28390, Pierce Biotechnology, Inc., Rockford, Ill.) was added to one well of each plate. Into each of the other two wells were added MES buffer and 1% benzyl quats (diluted from BARDAC.® 205M, from Lonza Inc., Fair Lawn, N.J.) as negative and positive controls, respectively. The plates were incubated overnight at 35° C.

Figure 4:
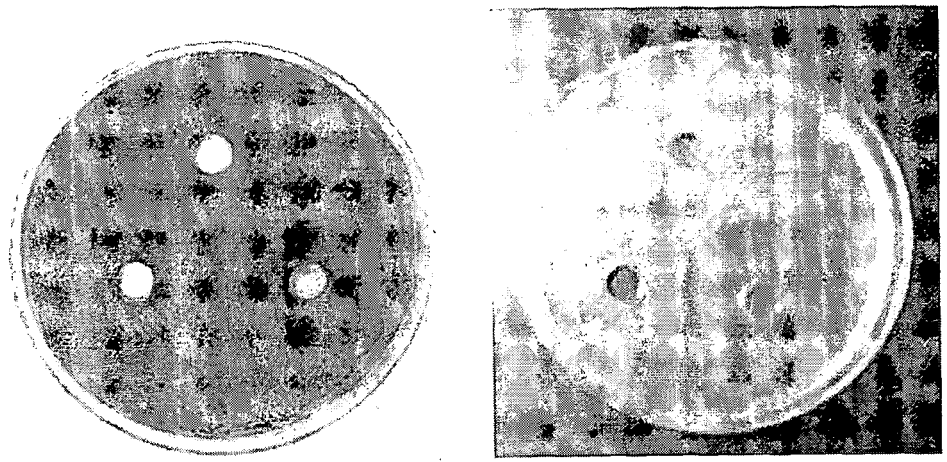
FIG. 4 shows representative pictures of zone-of-inhibition testing plates obtained in Example 8 for the growth of *Gardnerella vaginalis* (left) and *Lactobacillus acidophilus* (right)

The following day, the "zone of inhibition" for each sample was then measured for *Gardnerella vaginalis* and *Lactoba-* cillus acidophilus activity. The "zone of inhibition" is a circular zone formed around the agar plate in which the growth of the microorganism is inhibited. Absent treatment with an effective antimicrobial agent, the bacterial cells would normally produce an opaque lawn of growth. However, when growth is inhibited, a clear zone is observed. The diameter of this clear zone may thus be used as an indicator of antimicrobial effectiveness. The results are set forth below in Table 6 and shown in FIG. 4.

TABLE 6

Effect of xylitol on G. vaginalis and L. acidophilus, n = 2.

| Sample | Gardnerella vaginalis | Lactobacillus acidophilus |
|---|---|---|
| 5% xylitol | 4 mm | 0 mm |
| 1% benzyl quats | 5 mm | 15 mm |
| MES buffer | 0 mm | 0 mm |

As shown, xylitol inhibited *Gardnerella vaginalis*, but did not affect the growth of *Lactobacillus acidophilus*. The positive control, 1% Benzyl Quats, inhibited both microorganisms, while MES buffer itself had no effect on either of the two microorganisms.

EXAMPLE 9

Figure 5:
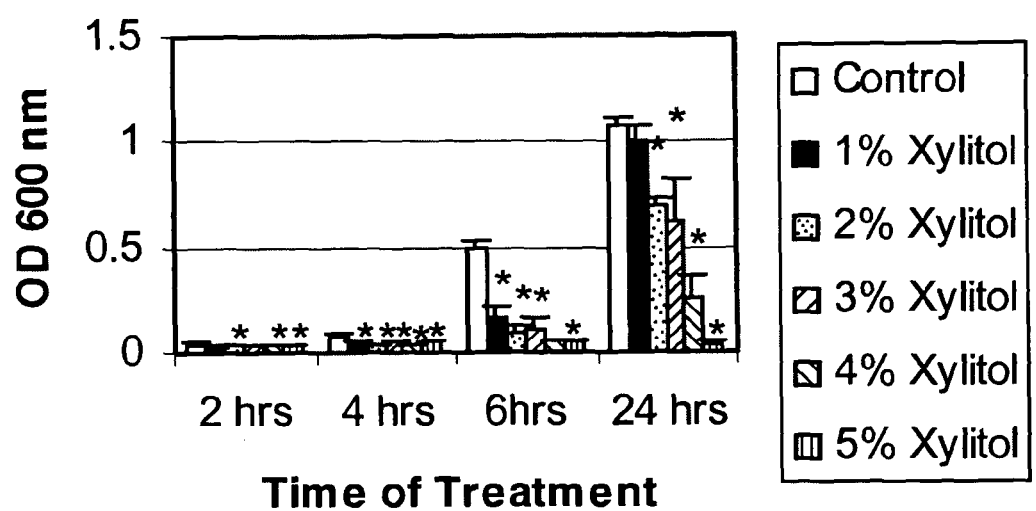
FIG. 5 presents optical density data obtained at $\lambda=600$ nm in Example 9 that shows the effects of xylitol on *Gardnerella Vaginalis* after 2, 4, 6, and 24 hours treatment (n=4, * represents P<0.05)
Figure 7:
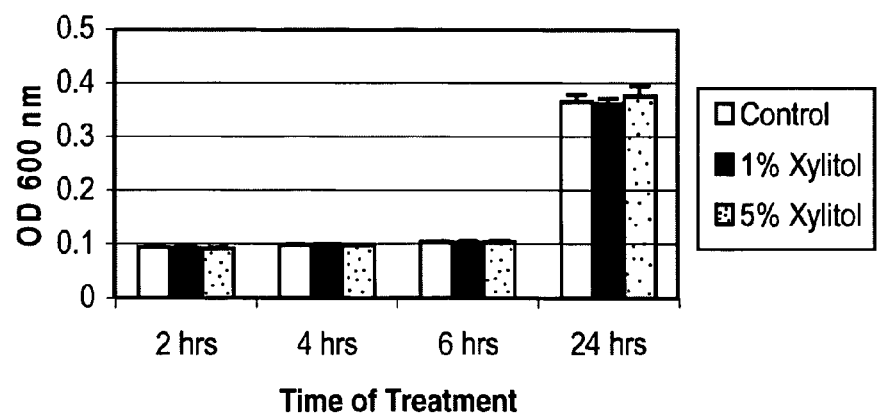
FIG. 7 presents optical density data obtained at $\lambda=600$ nm in Example 9 that shows the effects of xylitol on *Lactobacillus acidophilus* after 2, 4, 6, and 24 hours treatment (n=4)

Test compounds were dissolved in culture media to form a suspension. Control or xylitol solutions (0.9 milliliters) were filtered and added into culture tubes, and to this was added 0.1 milliliter of either the *Gardnerella vaginalis* or *Lactobacillus acidophilus* suspension at a concentration of around $10^6$ cfu/milliliter. The culture tubes were then incubated overnight at 37° C., whereafter the optical density was measured at 2, 4, 6 and 24 hours by pipetting 100 microliters of the control or sample solutions into 96-well microplates, and then using a ThermoMax Microplate Reader (Molecular Devices of Sunnyvale, Calif.) to obtain the optical density readings at 590 or 600 nm wavelengths. The results are shown in FIGS. 5 and 7. As shown in FIG. 5, xylitol exhibited significant inhibition on the growth of *Gardnerella vaginalis* as early as 2 hours after treatment. The inhibition effect remained evident throughout the 24-hour experimental period. In contrast, as shown in FIG. 7, xylitol did not exhibit any significant inhibition on the growth of *Lactobacillus acidophilus*.

EXAMPLE 10

Figure 6:
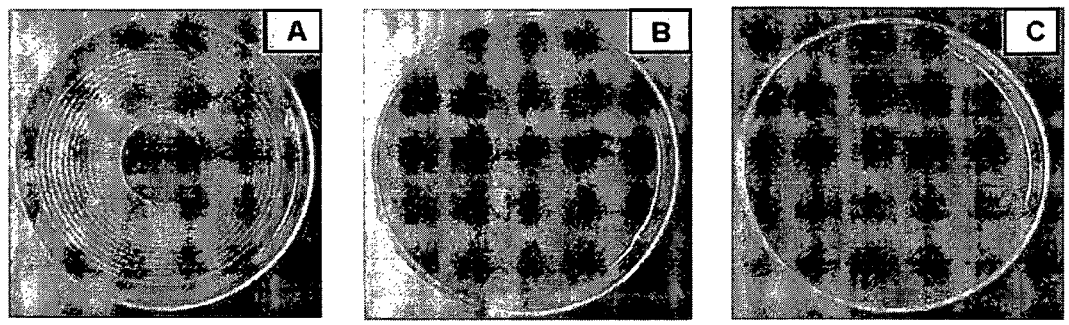
FIG. 6 shows representative pictures of testing plates obtained in Example 10 for the growth of *Gardnerella vaginalis* after 6 hours treatment (A—negative control; B—1% xylitol; C—5% xylitol)

Test compounds were dissolved in culture media to form a suspension. Control or xylitol solutions (0.9 milliliters) were filtered and added into culture tubes. To these solutions, 0.1 milliliter of the *Gardnerella vaginalis* or *Lactobacillus acidophilus* suspension was then added at a concentration of around $10^6$ cfu/milliliter. The culture tubes were incubated at 37° C. for 6 hours. The samples in the culture tubes were then diluted at 1, 10 and 100 times, and 100 microliters of each dilution was plated onto agar plates with WASP (Whitely Automatic Spiral Plate) spiral plating equipment from Don Whitely Scientific Limited, USA. The plates were incubated overnight at 35° C., and the numbers of colonies were counted on each plate by either ProtoCol® from Synbiosis, Frederick, Md., USA Whitely Scientific Limited, USA or by hand count. The results are shown below in Tables 7-8 and in FIG. 6.

TABLE 7

Effect of xylitol on G. Vaginalis, n = 4

| | Control | 1% xylitol | 2% xylitol | 3% xylitol | 4% xylitol | 5% xylitol |
|---|---|---|---|---|---|---|
| Plate Count | 2.32E+07 | *1.24E+05 | *1.64E+03 | *4.63E+02 | *1.03E+02 | *1.98E+01 |

*represents p < 0.05 compared to control group

TABLE 8

Effect of xylitol on L. acidophilus, n = 4

| | Control | 1% xylitol | 5% xylitol |
|---|---|---|---|
| Plate Count | 3.85 ± 0.44E+05 | 3.77 ± 0.49E+05 | 3.97 ± 0.36E+05 |

As indicated, all five concentrations exhibited significant inhibition of *Gardnerella vaginalis* growth compared to the control group. In contrast, xylitol did not exhibit any significant inhibition on the growth of *Lactobacillus acidophilus*.

EXAMPLE 11

Sorbitol, glucose, and xylitol were tested as described in Example 8. The results are show below in Table 9.

TABLE 9

Effect on G. vaginalis and L. acidophilus

| Sample | Gardnerella vaginalis | Lactobacillus acidophilus |
|---|---|---|
| 10% xylitol | 4 mm | 0 mm |
| 10% sorbitol | 0 mm | 0 mm |
| 10% glucose | 0 mm | 0 mm |
| 1% benzyl quats | 5 mm | 15 mm |
| MES buffer | 0 mm | 0 mm |

As indicated, xylitol exhibited an inhibitory effect on the growth of *Gardnerella vaginalis*, but not on *Lactobacillus acidophilus*.

EXAMPLE 12

Figure 8:
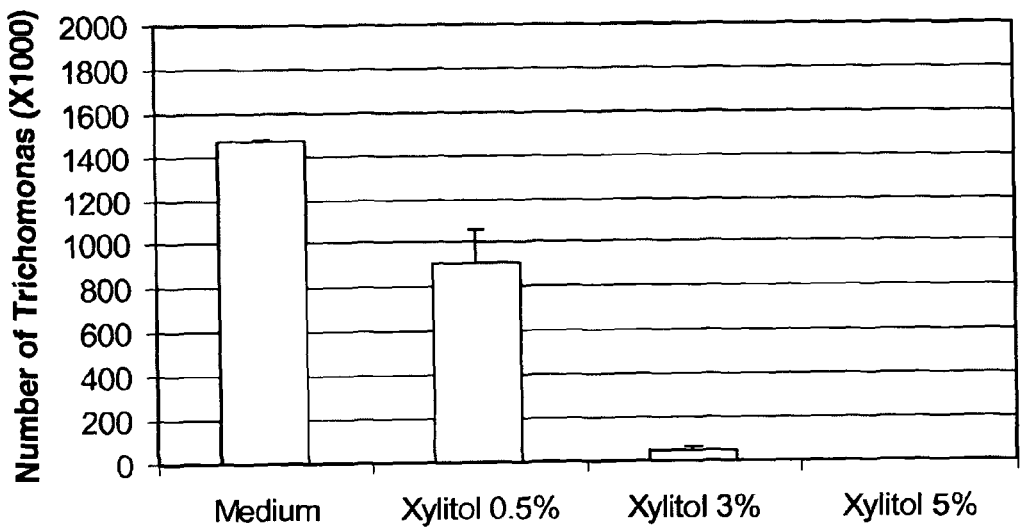
FIG. 8 is an organism count obtained in Example 12 that shows the effect of xylitol on *Trichomonas vaginalis* after 24 hours at concentrations of 0.5%, 3.0%, and 5.0%.
Figure 9:
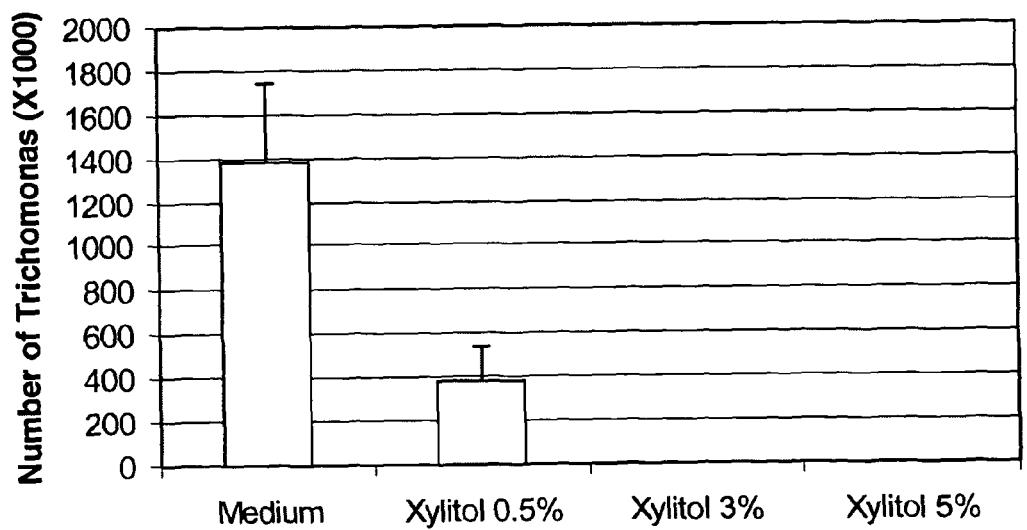
FIG. 9 is an organism count obtained in Example 12 that shows the effect of xylitol on *Trichomonas vaginalis* after 48 hours at concentrations of 0.5%, 3.0%, and 5.0%.

A sterile LYI-S-2 medium was prepared according to the manufacturer's instructions, and the pH of this medium was adjusted to pH 6.0 using 1 N HCl. Xylitol was then dissolved into the LYI-S-2 medium at concentrations of 0.5%, 3.0%, and 5.0% (wt/vol). 0.9 milliliters of xylitol and culture medium (as control) were also added into different culture tubes. Thereafter, 0.1 milliliter of *Trichomonas vaginalis* culture suspension (concentration of $1 \times 10^6$/milliliter) was added to each of the culture tubes, and then incubated at 35° C. on a 15 degree horizontal slant. The viable *Trichomonas vaginalis* cells in each tube were counted under a microscope after 24 and 48 hours. The above procedure was repeated four times for each concentration of xylitol and the control. The results are shown in FIGS. 8-9. As shown, xylitol significantly reduced the *Trichomonas vaginalis* cell count after 24 hours in comparison to the control group (FIG. 8). After 48 hours, xylitol had an even more significant inhibitory effect on the *Trichomonas vaginalis* cell count (FIG. 9). No live *Trichomonas vaginalis* cells were observed in the 3% and 5% xylitol treatment groups, while around 1.6 million *Trichomonas vaginalis* cells were counted in the control group.

EXAMPLE 13

Figure 10:
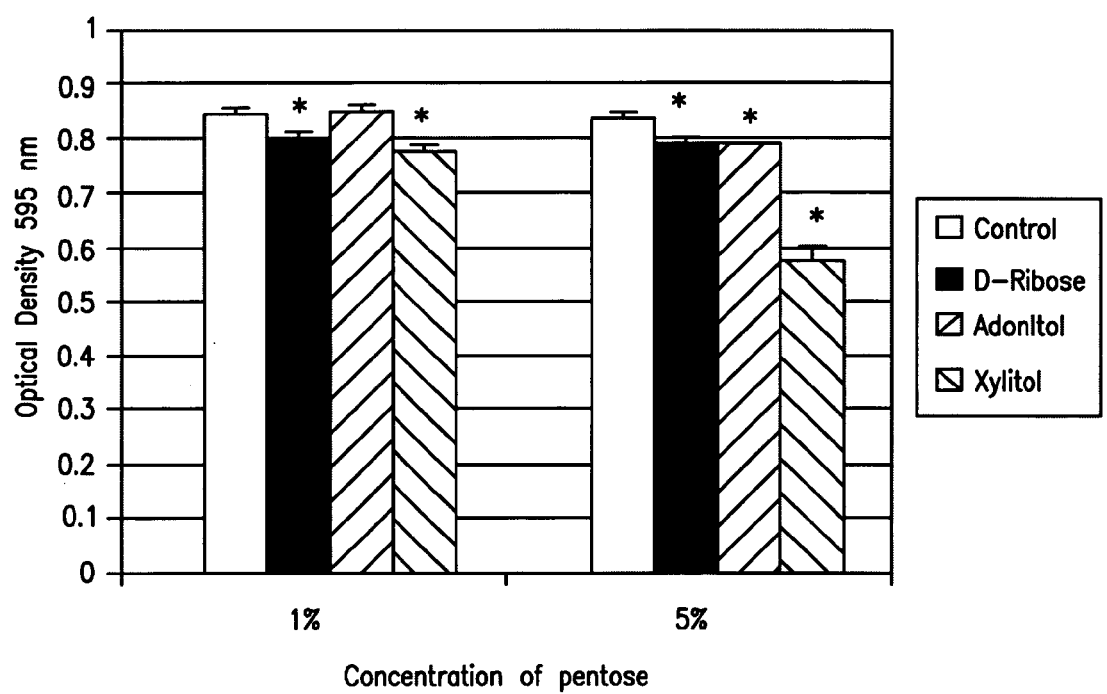
FIG. 10 is an optical density reading obtained at λ=595 nm in Example 13 that shows the effect of certain sugars and sugar derivatives on *Candida albicans* after 24 hours.

A YM culture medium was prepared according to the manufacturer's instructions, and the pH of this medium was adjusted to pH 6.0 using 1 N HCl. D-ribose (99%, Calbiochem), adonitol (99%, Alfa Aesar), and xylitol (98%, Danisco) were then dissolved into the YM medium at concentrations of 1.0% and 5.0% (wt/vol). 0.9 milliliters of the culture medium was also added into a different culture tube as a control. Thereafter, 0.1 milliliter of *Candida albicans* culture suspension (concentration of $1\times10^6$/milliliter) was added to each of the culture tubes, and then incubated overnight at 37° C. The viable *Candida albicans* cells in each tube were counted under a microscope after 24 hours. The above procedure was repeated four times for each concentration of the samples and the control. Thereafter, the optical density was measured for each sample at a wavelength of 590 nanometers. This was accomplished by pipetting 100 microliters of the control or sample solutions into 96-well agar plates, and then using a ThermoMax Microplate Reader from Molecular Devices of Sunnyvale, Calif. to obtain the optical density readings. The results are shown in FIG. 10. As shown, the sugar and sugar-based compounds reduced the *Candida albicans* cell count after 24 hours in comparison to the control group.

EXAMPLE 14

Figure 11:
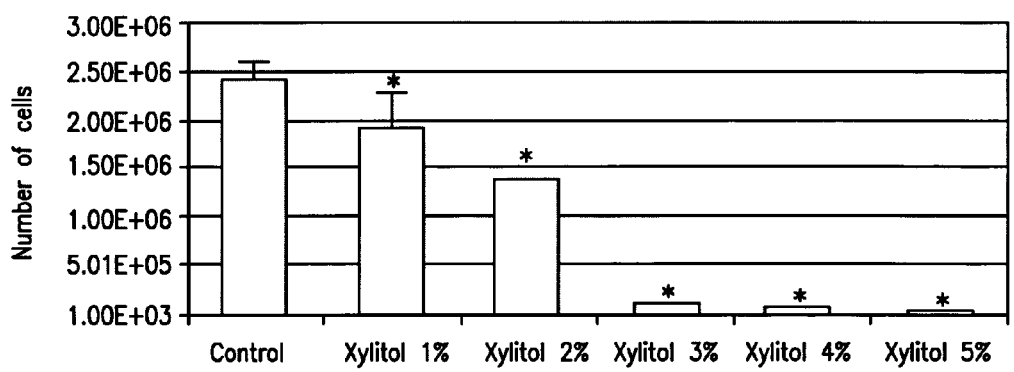
FIG. 11 is a plate count number obtained in Example 14 that shows the effect of xylitol on *Candida albicans* after 24 hours.

A YM culture medium was prepared according to the manufacturer's instructions, and the pH of this medium was adjusted to pH 6.0 using 1 N HCl. Xylitol was then dissolved into the YM medium at concentrations of 1%, 2%, 3%, 4%, and 5.0% (wt/vol). 0.9 milliliters of the culture medium were also added into a different culture tube as a control. Thereafter, 0.1 milliliter of *Candida albicans* culture suspension (concentration of $1\times10^6$/milliliter) was added to each of the culture tubes, and then incubated at 37° C. The viable *Candida albicans* cells in each tube were counted under a microscope after 24 hours. The above procedure was repeated four times for each concentration and the control. The results are shown in FIG. 11. As shown, xylitol significantly reduced the *Candida albicans* cell count after 24 hours in comparison to the control group.

EXAMPLE 15

Figure 12:
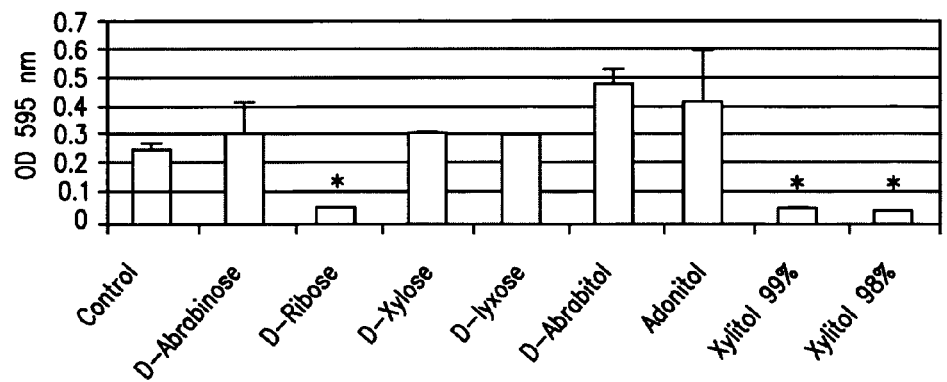
FIG. 12 is an optical density reading obtained at λ=595 nm in Example 15 that shows the effect of certain sugars and sugar derivatives on *Gardnerella vaginalis* after 24 hours.

A growth medium for *Gardnerella vaginalis* was prepared according to the manufacturer's instructions, and the pH of this medium was adjusted to pH 6.0 using 1 N HCl. D-ribose (99%, Calbiochem), D-arabinose (98%, Alfa Aesar), D-xylose (Aldrich), D-lyxose (99%, Avovado), D-arabitol (97%, Alfa Aesar), adonitol (99%, Alfa Aesar), xylitol (99%, Alfa Aesar), xylitol (98%, Danisco), and xylitol (98%, Aldrich) were then dissolved into the growth medium at a concentration of 1.0% (wt/vol). 0.9 milliliters of the culture medium was also added into a different culture tube as a control. Thereafter, 0.1 milliliter of *Gardnerella vaginalis* culture suspension (concentration of $1\times10^6$/milliliter) was added to each of the culture tubes, and then incubated overnight at 37° C., and the optical density was then measured after 24 hours at a wavelength of 595 nanometers. This was accomplished by pipetting 100 microliters of the control or sample solutions into 96-well microplates, and then using a ThermoMax Microplate Reader from Molecular Devices of Sunnyvale, Calif. to obtain the optical density readings. The results are depicted in FIG. 12. As shown, xylitol and D-ribose significantly reduced the *Gardnerella vaginalis* cell count after 24 hours in comparison to the control group. Although the remaining compounds did not have a significant effect on the *Gardnerella vaginalis* cell count in this example, it is nevertheless believed that such compounds may be effective under other conditions, such as at higher concentrations.

EXAMPLE 16

An alkyl polyglycoside (APG) surfactant was obtained from Dow Chemical Co. of Midland, Mich. under the name "Triton™ CG-110." The Triton™ CG-110 surfactant was diluted to a concentration of 10 mg/ml using a 1× sterilized buffer solution (pH=4.7) of (2-[N-morpholino] ethane sulfonic acid ("MES")). For testing, a suspension of *Candida albicans* (ATCC #10231) was prepared by diluting a $1\times10^8$ colony forming unit (cfu) per milliliter (ml) stock of *Candida albicans* with a TSB solution to a concentration of $1\times10^5$ cfu/ml. One milliliter of the suspension was applied to Dextrose Sabouraud agar plates, and allowed to grow at 35° C. for 4 hours. 4-millimeter diameter wells were then punched in each agar plate, and 100 microliters of the sample was added to the wells. As a negative control, a 1×MES (pH=4.7) buffer was employed. Further, as a positive control, a solution was employed that contained a benzyl quaternary ammonium chloride antimicrobial agent (diluted from BARDAC.® 205M, from Lonza Inc., Fair Lawn, N.J.) at a concentration of 10 mg/ml. The plates were incubated overnight at 35° C. After 24 hours, the "zone of inhibition" for each sample was measured. The zone of inhibition for (1) the positive control was 10 millimeters, (2) the negative control was 0 millimeters, and (3) the test sample was 3 millimeters. Thus, the saccharide-based nonionic surfactant inhibited the growth of *Candida albicans*.

EXAMPLE 17

The ability to inhibit pathogenic growth in accordance with the present invention was demonstrated. Specifically, the procedure of Example 15 was repeated for *Gardnerella vaginalis* (ATCC # 14018). The zone of inhibition for (1) the positive control (benzyl quaternary ammonium chloride, concentration of 5 mg/ml) was 4 millimeters, (2) the negative control was 0 millimeters, and (3) the test sample was 7 millimeters. Thus, not only did the saccharide-based nonionic surfactant inhibit the growth of *Gardnerella vaginalis*, but it also performed better than the conventional benzyl quaternary ammonium antimicrobial agent.

EXAMPLE 18

An alkyl polyglycoside (APG) surfactant was obtained from Dow Chemical Co. of Midland, Mich. under the name "Triton™ CG-110." The Triton™ CG-110 surfactant was diluted to concentrations of 1 mg/ml and 5 mg/ml using a 1× sterilized MES buffer (pH=4.7). 0.9 milliliters of the surfactant solutions were then added to culture tubes. For testing, a suspension of *Candida albicans* (ATCC #10231) was prepared by diluting a 1×10⁸ colony forming unit (cfu) per milliliter (ml) stock of *Candida albicans* with a TSB solution to a concentration of 1×10⁶ cfu/ml. 0.1 milliliters of the suspension was then added to each culture tube, and allowed to grow at 35° C. for 30 minutes. The samples in the culture tubes were then diluted at 1, 10 and 100 times, and 100 microliters of each dilution was plated onto agar plates with WASP (Whitely Automatic Spiral Plate) spiral plating equipment from Don Whitely Scientific, Ltd. The plates were incubated overnight at 35° C., and the colonies were counted on each plate by either ProtoCol® from Synbiosis of Frederick, Md. or by hand count. As a negative control, a 1×MES (pH=4.7) buffer was also employed in the same manner described above. Duplicate tests were conducted for each compound and control. The results are set forth below in Table 10.

TABLE 10

*Candida albicans* Reduction Results

| Sample | Average count per ml | % Reduction |
|---|---|---|
| 5 mg/ml APG | $0.00 \times 10^0$ | 100.0% |
| 1 mg/ml APG | $2.00 \times 10^3$ | 99.8% |
| Control | $1.32 \times 10^6$ | 0.0% |

As indicated, good inhibition for *Candida albicans* was achieved even for the relatively low concentration of 1 mg/ml APG.

EXAMPLE 19

Initially, sterile LYI-S-2 media (AYCC medium 2152) was provided and adjusted to a pH of 6.0 using 1 N HCl. Thereafter, an alkyl polyglycoside (APG) surfactant was diluted into the LYI-S-2 media to concentrations of 5 mg/ml, 30 mg/ml, and 50 mg/ml. The surfactant was obtained from Dow Chemical Co. of Midland, Mich. under the name "Triton™ CG-110." 0.9 milliliters of the surfactant solutions were then added to screw-capped test tubes. For testing, a suspension of *Trichomonas vaginalis* (ATCC #30001) was prepared by diluting a 2.16×10⁶ colony forming unit (cfu) per milliliter (ml) stock with a LYI-S-2 media to a concentration of 1×10⁶ cfu/ml. 0.1 milliliters of the suspension was then added to each test tube, and allowed to grow at 35° C. for 24 hours on a 150 horizontal slant. As a negative control, a LYI-S-2 media was also employed in the same manner described above. The test was repeated four (4) times for the test and control samples. The results are set forth below in Table 11.

As indicated, good inhibition for *Trichomonas vaginalis* was achieved.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A vaginal treatment composition comprising:
at least one low acyl gellan gum capable of forming a gel in the presence of monovalent or polyvalent cations;
xylitol in an amount of from about 0.01 wt/vol % to about 20 wt/vol %; and
At least one phenolic acid selected from the group consisting of p-hydrobenzoic acid, protocatechuic acid, vanillic acid, chlorogenic acid, caffeic acid, ferulic acid, gallic acid, sinapic acid, syringic acid, coumaric acid, cinnamic acid, gentisic acid, salicylic acid, veratric acid, anisic acid, crotonic acid, hydroxy benzoic acid, hydroxy phenyl acetic acids, and combinations thereof;
wherein the vaginal treatment composition has an osmolarity of from about 270 to about 310 milliosmoles per liter and a pH of from about 2.5 to about 5.0, and
wherein the composition lacks monovalent and divalent salts in an amount sufficient for gelation, such that a gel is formed only after the composition is delivered to the vaginal of a female.

2. The vaginal treatment composition of claim 1, wherein the gellan gum is present in the composition in an amount of from about 0.01 wt/vol % to about 10 wt/vol %.

3. The vaginal treatment composition of claim 1, wherein the gellan gum is present in the composition in an amount of from about 0.1 wt/vol % to about 1 wt/vol %.

4. The vaginal treatment composition of claim 1, wherein the gellan gum has a degree of deacylation of at least about 20%.

5. The vaginal treatment composition of claim 1, wherein the gellan gum has a degree of deacylation of at least about 50%.

6. The vaginal treatment composition of claim 1, wherein the gellan gum is nonaclyated.

7. The vaginal treatment composition of claim 1, wherein the gellan gum has a gelation temperature within the range 30° C. to 50° C.

TABLE 11

Average count per ml of *Trichomonas vaginalis*

| Sample | Run 1 | Run 2 | Run 3 | Run 4 | Mean | % Reduction |
|---|---|---|---|---|---|---|
| 5 mg/ml APG | 0 | 0 | 0 | 0 | 0 | 100.0 |
| 30 mg/ml APG | 0 | 0 | 0 | 0 | 0 | 100.0 |
| 50 mg/ml APG | 0 | 0 | 0 | 0 | 0 | 100.0 |
| Control | $1.516 \times 10^6$ | $1.520 \times 10^6$ | $1.460 \times 10^6$ | $1.400 \times 10^6$ | $1.474 \times 10^6$ | 0.0 |

8. The vaginal treatment composition of claim 1, wherein xylitol is present in the composition in an amount of from about 0.1 wt/vol % to about 10 wt/vol %.

9. The vaginal treatment composition of claim 1, wherein the phenolic acid is gallic acid.

10. The vaginal treatment composition of claim 1, wherein phenolic acids constitute from 0.001 wt/vol % to about 5 wt/vol % of the composition.

11. The vaginal treatment composition of claim 1, wherein phenolic acids constitute from 0.01 wt/vol % to about 0.25 wt/vol % of the composition.

12. The vaginal treatment composition of claim 1, wherein the composition has an osmolarity of from about 280 to about 300 milliosmoles per liter.

13. The vaginal treatment composition of claim 1, wherein the composition has a pH of from about 3.0 to about 4.5.

14. The vaginal treatment composition of claim 1, further comprising at least one nonionic tonicity agent.

15. The vaginal treatment composition of claim 1, wherein the vaginal treatment composition does not substantially inhibit the growth of *Lactobacillus acidophilus*.

* * * * *